(12) United States Patent
Hara

(10) Patent No.: US 6,965,031 B2
(45) Date of Patent: Nov. 15, 2005

(54) PROCESS FOR PRODUCING (3R,5S)-(E)-7-[2-CYCLOPROPYL-4-(4-FLUOROPHENYL)-QUINOLIN- 3-YL]-3,5-DIHYDROXYHEPT-6-ENIC ACID ESTERS

(75) Inventor: Mari Hara, Yokohama (JP)

(73) Assignees: Mitsubishi Chemical Corporation, Tokyo (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/629,865

(22) Filed: Jul. 30, 2003

(65) Prior Publication Data

US 2004/0030139 A1 Feb. 12, 2004

Related U.S. Application Data

(63) Continuation of application No. PCT/JP02/00835, filed on Feb. 1, 2002.

(30) Foreign Application Priority Data

Feb. 2, 2001 (JP) .................................... 2001-026316
Oct. 29, 2001 (JP) .................................... 2001-331480

(51) Int. Cl.$^7$ ........................................... C07D 453/02
(52) U.S. Cl. ..................................................... 546/136
(58) Field of Search ......................................... 546/136

(56) References Cited

FOREIGN PATENT DOCUMENTS

EP 0 304 063 2/1989

(Continued)

OTHER PUBLICATIONS

Takeshi Hanamoto et al., "A Facile Entry to β,δ–Diketo and syn–β,δ Dihydroxy Esters", Tetrahedron Letters, vol. 29, No. 49, pp. 6467–6470, 1988.

(Continued)

*Primary Examiner*—Taofiq Solola
*Assistant Examiner*—Robert Shiao
(74) *Attorney, Agent, or Firm*—Wenderoth, Lind & Ponack, L.L.P.

(57) ABSTRACT

A process for producing a compound represented by the following formula (IV):

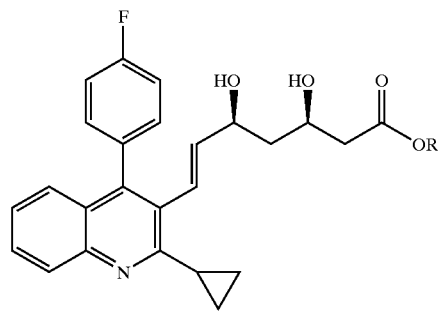

IV (wherein R denotes a hydrogen atom, an alkyl group, or an aryl group), comprising reducing a compound selected from the group consisting of:
a compound represented by the following formula (I):

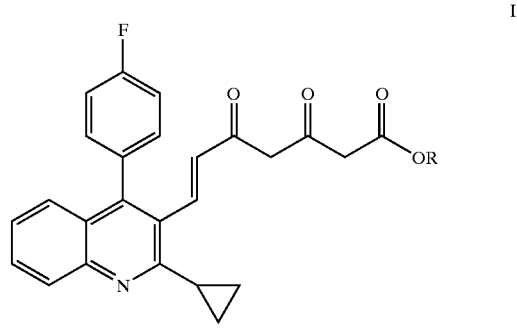

I (wherein R is as defined in the formula);
a compound represented by the following formula (II):

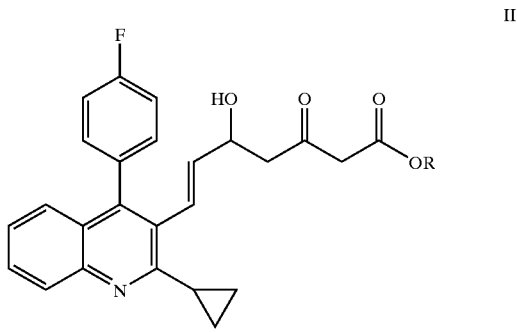

II (wherein R is as defined in the formula); and
a compound represented by the following formula (III):

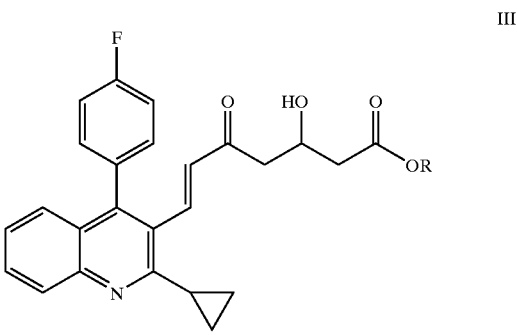

III (wherein R is as defined in the formula), by reacting the compound with a cell of a microorganism and/or a cell preparation thereof capable of stereo-selectively reducing a keto group.

13 Claims, No Drawings

FOREIGN PATENT DOCUMENTS

| | | |
|---|---|---|
| EP | 0 569 998 | 11/1993 |
| JP | 5-178841 | 7/1993 |
| JP | 5-308977 | 11/1993 |
| JP | 8-92217 | 4/1996 |
| JP | 8-127585 | 5/1996 |
| JP | 11-507204 | 6/1999 |

OTHER PUBLICATIONS

Barry Lygo, "N–Acyl–2–methylaziridines: Synthesis and Utility in the C–Acylation of β–Ketoester Derived Dianions", Tetrahedron, vol. 51, No. 47, pp. 12859–12868, 1995.

James S. Hubbard et al., "Condensations at the 6 Position of the Methyl Ester and the Dimethylamide of 3,5–Dioxohexanoic Acid via 2,4,6–Trianions", J. Org. Chem., vol. 46, No. 12, pp. 2566–2570, 1981.

S. Nagamatsu et al., "Chiral separation of a pharmaceutical intermediate by a simulated moving bed process", Journal of Chromatography A, 832, 55–65, (1999).

A. Shafiee et al., "Purification, characterization and immobilization of an NADPH–dependent enzyme involved in the chiral specific reduction of the keto ester M, an intermediate in the synthesis of an anti–asthma drug, Montelukast, from Microbacterium campoquemadoensis (MB5614)", Appl. Microbiol Biotechnol, 49, pp. 709–717, 1998.

Biswanath Das et al., "The First Conversion of Camptothecin To (S)–Mappicine By An Efficient Chemoenzymatic Method", Bioorganic & Medicinal Chemistry Letters, 8, pp. 1403–1406, 1998.

Ramesh N. Patel et al., "Enantioselective microbial reduction of 3,5–dioxo–6–(benzyloxy) hexanoic acid, ethyl ester", Enzyme Microb. Technol., vol. 15, pp. 1014–1021, 1993.

US 6,965,031 B2

PROCESS FOR PRODUCING (3R,5S)-(E)-7-[2-CYCLOPROPYL-4-(4-FLUOROPHENYL)-QUINOLIN- 3-YL]-3,5-DIHYDROXYHEPT-6-ENIC ACID ESTERS

This application is a Continuation application of PCT/JP02/00835, filed Feb. 1, 2002.

TECHNICAL FIELD

The present invention relates to a novel process for producing (3R, 5S)-(E)-7-[2-cyclopropyl-4-(4-fluorophenyl)-quinolin-3-yl]-3,5-dihydroxyhept-6-enic acid esters. This compound is useful as a synthetic intermediate of "3-hydroxy-3-methylglutaryl CoA-reductase inhibitor" disclosed in JP 1-279866 A as being useful for a blood-cholesterol reducer.

In addition, the present invention relates to a novel process for producing β-diketocarboxylate ester derivative, which is required for synthesis of (3R, 5S)-(E)-7-[2-cyclopropyl-4-(4-fluorophenyl)-quinolin-3-yl]-3,5-dihydroxyhept-6-enic acid esters as described above.

BACKGROUND ART

As a process for chemically producing (3R, 5S)-(E)-7-[2-cyclopropyl-4-(4-fluorophenyl)-quinolin-3-yl]-3,5-dihydroxyhept-6-enic acid esters, for example, the following production route has been known as disclosed in JP 1-279866 A and Journal of Chromatography A, 832 (1999) p55–65.

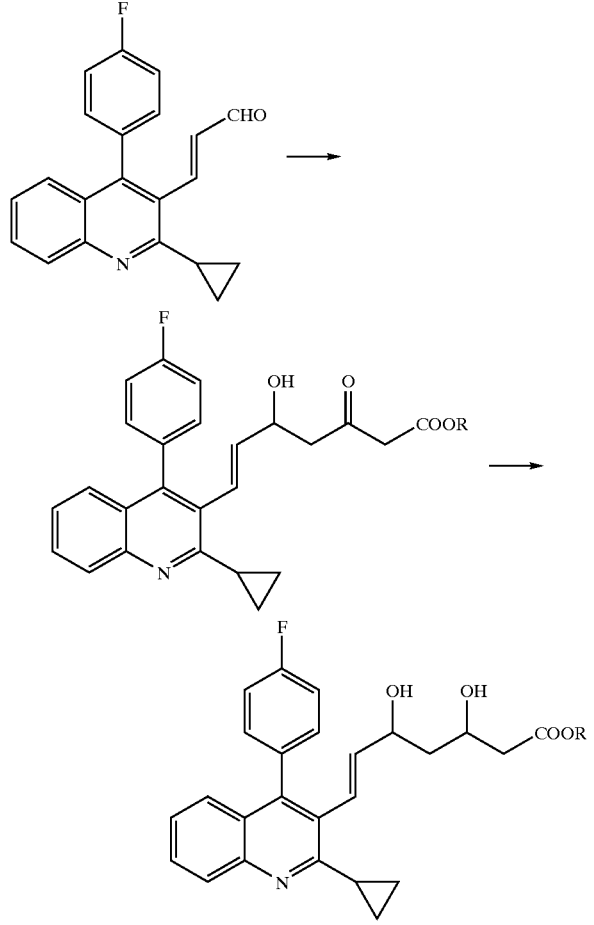

In these processes, however, a reaction product is a mixture of an optical isomer and an optically active substance, so that only the desired optically active substance compound should be obtained through separation and purification by means of chromatography and so on in their respective final steps. It is rather difficult to say that the isolation of an isomer in the final step is cost effective and efficient on an industrial scale.

Furthermore, in JP 8-92217 A, there is disclosed another production process using an optically active Schiff base.

Still furthermore, in JP 8-127585 A, there is disclosed a production process using methyl (R)-3-tert-butyl dimethylsilyloxy-6-dimethoxyphosphinyl-5-oxohexanoate at a very low temperature.

On the other hand, as a process for producing an optically active alcohol product by a stereo-selective reduction of a compound having a keto group using microbial cells and/or a cell preparation thereof, in Appl. Microbiol. Biotechnol. (1998) 49: p. 709–717, there is a description that the following chemical reaction can be performed using Microbacterium campoquemadoensis strain MB5614.

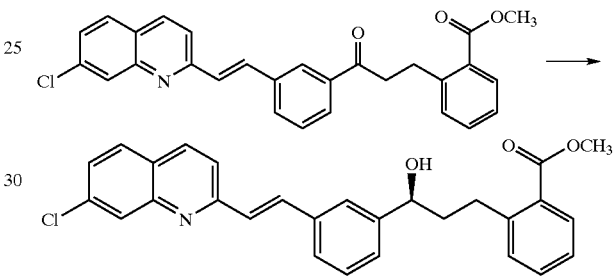

Furthermore, in Bioorg. Med. Chem. Lett., vol. 8, p1403-(1998), there is a description that the following reaction can be performed using a bakers yeast.

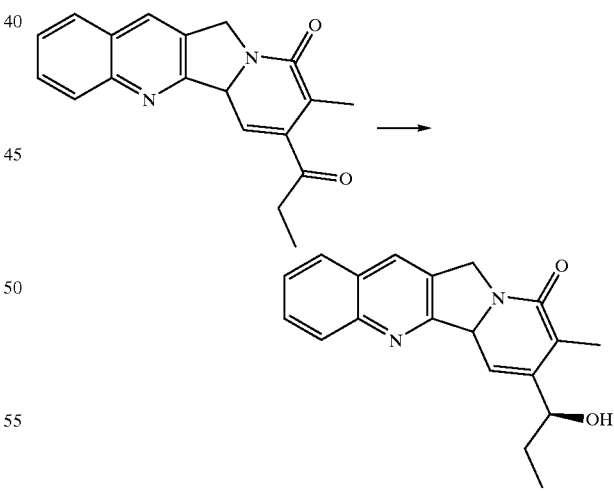

However, with respect to a compound in which carbonyl groups continuously exist in the molecule thereof in addition to the presence of olefin on the á-position of the carbonyl group, such as (E)-7-[2-cyclopropyl-4-(4-fluorophenyl)-quinolin-3-yl]-3,5-dihydroxyhepto-6-enoic acid esters, any example in which such a compound can be reduced using a microorganism in a stereo-selective manner has not been known in the art.

DISCLOSURE OF THE INVENTION

Therefore, it has been desired to develop a novel production process which is capable of cost-effectively producing (3R,5S)-(E)-7-[2-cyclopropyl-4-(4-fluorophenyl)-quinolin-3-yl]-3,5-dihydroxyhept-6-enic acid esters on an industrial scale.

For solving the above problem, the inventors of the present invention have made extensive studies over and over again and found out that the desired products can be obtained at high optical purities when the compounds represented by the following compounds (I) to (III) and (II') and (III') are used as raw materials, resulting in accomplishment of the present invention. Therefore, a gist of the present invention resides in a process for producing a compound represented by the following formula (IV):

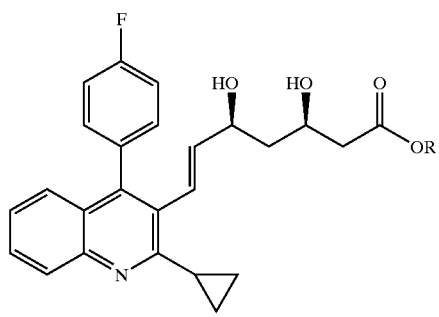

(where R denotes a hydrogen atom, an alkyl group, or an aryl group), comprising reducing a compound selected from the group consisting of:
a compound represented by the following formula (I):

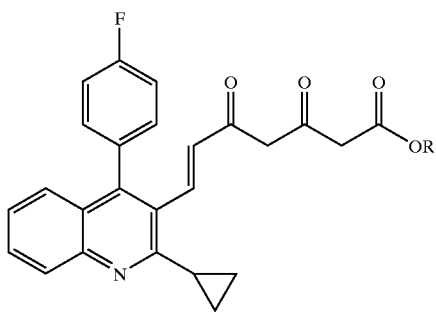

(where R is as defined in the formula);
a compound represented by the following formula (II):

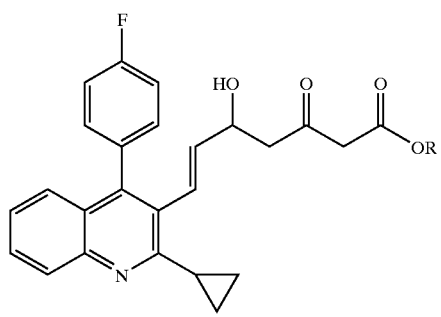

(where R is as defined in the formula); and
a compound represented by the following formula (III):

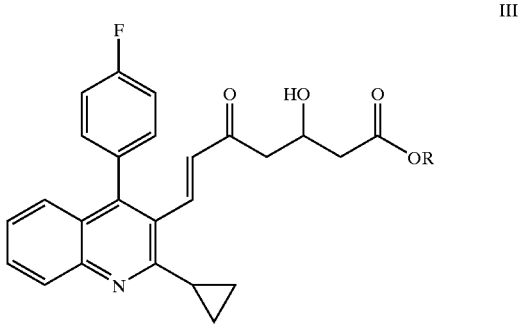

(where R is as defined in the formula), by reacting the compound with a cell of a microorganism and/or a cell preparation thereof capable of stereo-selectively reducing a keto group.

Further, another gist of the present invention resides in a process for producing the compound (I), comprising conducting a condensation reaction between 2-cyclopropyl-4-(4-fluorophenyl) quinolin-3-carbaldehyde represented by the following formula (A):

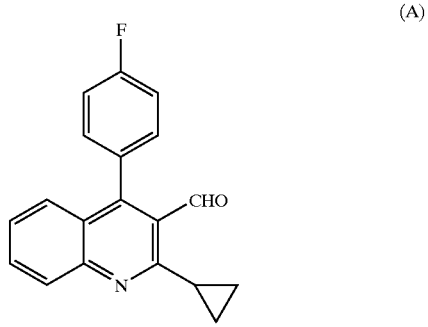

and a compound represented by the following formula (B):

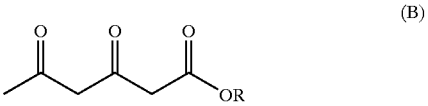

(where R denotes a hydrogen atom, an alkyl group, an aralkyl group, or an aryl group).

BEST MODE FOR CARRYING OUT THE INVENTION

Hereinafter, the present invention will be described in detail.

According to the present invention, a process for producing (3R,5S)-(E)-7-[2-cyclopropyl-4-(4-fluorophenyl)-quinolin-3-yl]-3,5-dihydroxyhept-6-enic acid esters coma compound represented by the following formula (I)

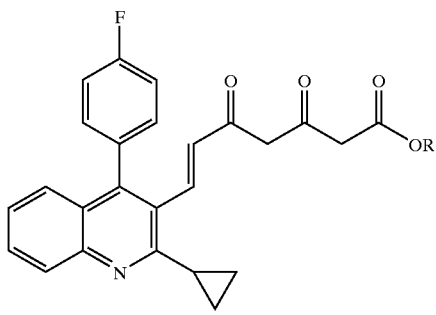

(where R denotes a hydrogen atom, an alkyl group, or an aryl group);
a compound represented by the following formula (II)

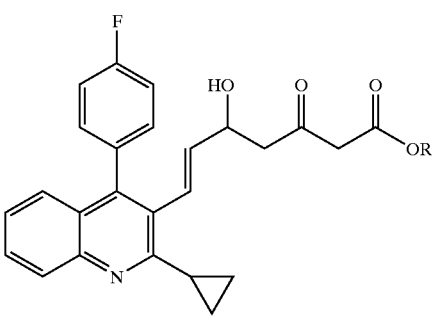

(where R is as defined in the formula); and
a compound represented by the following formula (III)

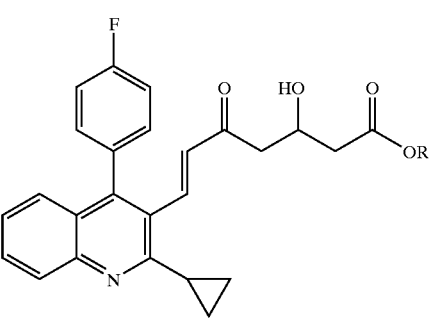

(where R is as defined in the formula), by reacting the compound with a cell of a microorganism and/or a cell preparation thereof capable of stereo-selectively reducing a keto group.

In the compounds represented by the above formulae (I) to (III), which are raw materials to be used in the production process of the present invention, R represents a hydrogen atom, an alkyl group, or an aryl group.

The alkyl group may be an alkyl group such as an methyl group, an ethyl group, an isopropyl group, a cyclopropyl group, a butyl group, an isobutyl group, a t-butyl group, a cyclohexyl group, a benzyl group, or a phenethyl group, or a straight-, branched-, or cyclic-alkyl group which may be substituted with an aryl group.

The aryl group may be a phenyl group or a naphthyl group which may be substituted with an alkyl group, such as a phenyl group, a mesityl group, or a naphthyl group.

The above R is preferably a $C_1$–$C_4$ alkyl group, a benzyl group, or a phenyl group, more preferably a $C_1$–$C_4$ alkyl group, particularly preferably a methyl group or an ethyl group.

According to the production process of the present invention, the compounds represented by the formulae (II) and (III) may be respectively optically active substances represented by the following formula (II')

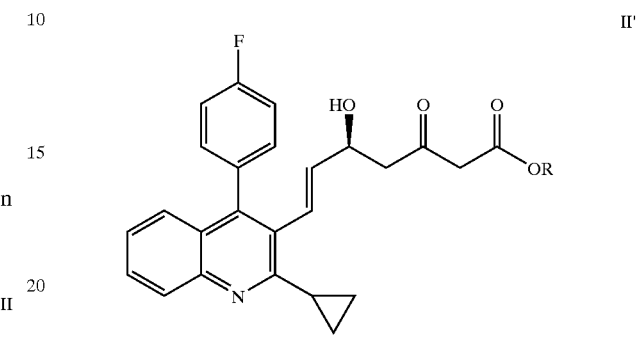

(where R is as defined in the formula), and the following formula (III')

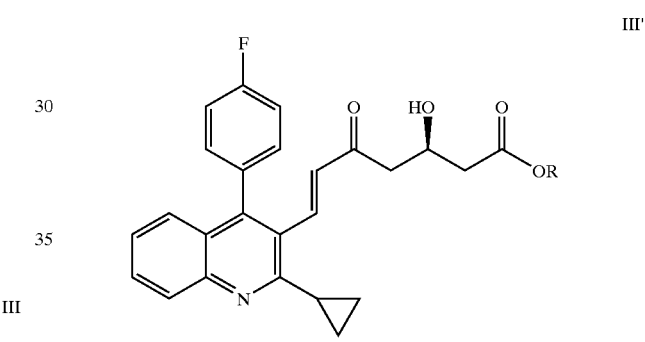

(where R is as defined in the formula).

The compounds represented by the formula (I) to (III) and (II') and (III') can be optionally produced with a combination of a process disclosed in JP 1-279866 A, JP 8-127585 A, JP 5-178841 A, or the like and a process well known in the art.

Further, as a preferable process for producing the compound represented by the formula (I), the inventors of the present invention have reached the following process in which the compound is obtained by a condensation reaction between
2-cyclopropyl-4-(4-fluorophenyl) quinolin-3-carbaldehyde represented by the following formula (A):

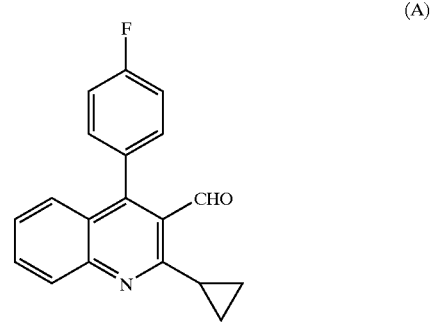

and a compound represented by the following formula (B):

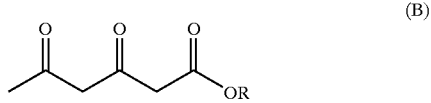

(B)

(where R denotes a hydrogen atom, an alkyl group, an aralkyl group, or an aryl group). By employing this process, the compound represented by the above formula (I) can be produced easily and efficiently.

A condensation reaction between the compound (A) and the compound (B) can be progressed by the same operation as that of one which is a so-called aldol reaction. In general, a process, by which a base is added in a solution containing the compound (B) and a solution containing the compound (A) is then dropped into the solution under a nitrogen or inert-gas atmosphere, is preferably performed.

The bases to be used in the above condensation reaction include: hydrides of alkali metals or alkaline-earth metals, such as sodium hydride, potassium hydride, and calcium hydride; lithium alkyl reagents such as n-butyl lithium and t-butyl lithium; Grignard reagents such as t-butyl magnesium chloride; alkali-metal alkoxides such as sodium ethoxide; and $NaNH_2$. In addition, solid bases of alkaline-earth metal oxides or the like such as magnesium oxide may be included. Among them, hydrides of alkali metals or alkali-earth metals, and $NaNH_2$ are preferable, alkali-metal hydrides are more preferable, and sodium hydride is particularly preferable.

In general, the usage amount of the base is 1.5 equivalent weights or more, preferably 2 equivalent weights or more with respect to the compound (B). If it is excessively used, a side reaction may occur and a reduction in yield may thus occur. Therefore, in general, it is used in the range of 10 equivalent weights or less. In the above range, it is preferably in the range of 2 to 3 equivalent weights, particularly preferably 2 to 2.7 equivalent weights.

The reaction is generally performed using a solvent. The solvents to be used include: aromatic hydrocarbon solvents such as toluene, benzene, and xylene; ether solvents such as methyl-t-butyl ether, dimethoxy ethane, and tetrahydrofuran; halogenated hydrocarbon solvents such as methylene chloride; and non-protonic solvents such as N,N-dimethyl formamide. Among them, a preferable solvent is one having a dielectric constant of 2.5 or more, more preferably 5 or more at 20° C. Specific examples of the above preferable solvent include tetrahydrofuran, dimethoxy ethane, N,N-dimethyl formamide, and N,N-dimethyl imidazolidinone, and tetrahydrofuran is particularly preferable.

The usage amount of the solvent is generally about 0.5 to 100-fold volume of a reaction substrate. In this range, from an industrial viewpoint, it is preferable to adopt the range of 20-fold volume or less.

As a reaction operation, the compound (A) may be added after mixing the base and the compound (B), a mixture between the base and the compound (B) may be added in the compound (A), a mixture between the compounds (A) and (B) may be added in the base, or the base may be added in a mixture between the compounds (A) and (B). In any operation, the reaction can proceed. However, a preferable process is to mix the base and the compound (B) and then add the compound (A) in the mixture.

The reaction may proceed at a temperature of −50° C. to 100° C., preferably −20° C. to 40° C., typically for 30 minutes or more, preferably 1 hour or more. If required, the temperature may be increased.

After termination of the reaction, after terminating the reaction by adding water, acetic acid, ammonium chloride, or the like in a reaction system, the compound (I) can be obtained by conventional isolation and purification operations, such as washing with water and separatory extraction.

In the condensation reaction between the compound (A) and the compound (B), by selecting the base and the solvent to be used, the compound (I) can also be produced after providing a compound [hereinafter, referred to as compound (C)], represented by the following general formula (C):

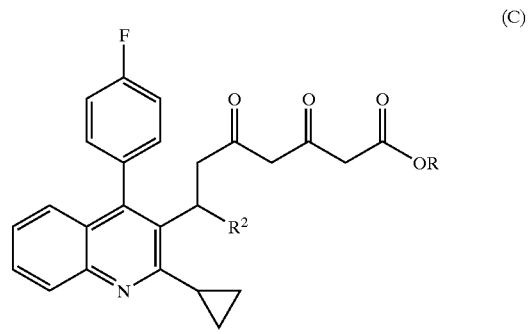

(C)

(where R is as defined in the formula, and $R^2$ is a hydroxyl group, a halogen group, a silyloxy group, a sulfonyloxy group, an acyloxy group, an alkoxycarbonyloxy group, an alkylthiocarbonyloxy group, an alkoxythiocarbonyloxy group, or an alkylthiothiocarbonyloxy group) or a salt thereof as an intermediate of the production.

In the above-mentioned compound (C), R can use the same previously mentioned groups. Further, $R^2$ denotes: a hydroxyl group; a halogen atom such as a chorine atom and a bromine atom; silyloxy groups such as trimethyl silyloxy group and t-butyldimethyl silyloxy group; sulfonyloxy groups such as methanesulfonyloxy group and paratoluene sulfonyloxy group; acyloxy groups such as acetoxy group and propionyloxy group; alkoxycarbonyloxy groups such as methoxycarbonyloxy group and vinyloxycarbonyloxy group; alkylthiocarbonyloxy groups such as methylthiocarbonyloxy group; alkoxythiocarbonyloxy groups such as methoxythiocarbonyloxy group; or alkylthiothiocarbonyloxy groups such as methylthiothiocarbonyloxy group. Of these groups, a hydroxyl group, a sulfonyloxy group or an acyloxy group is preferable, an acyloxy group is more preferable and an acetoxy group is particularly preferable.

A preferable combination of substituents to be provided as the compound (C) described above may be a combination of R and $R^2$ as the preferable ones, which are mentioned in the description of the above substituents.

One of the specific reaction steps when the above compound (C) is used as an intermediate will be described below. An intermediate having the above $R^2$ as a hydroxyl group in the compound (C) is obtained, for example by the use of a combination of NaH and n-BuLi as a base to be used in a condensation reaction between the compound (A) and the compound (B). In addition, the compound (I) can be obtained by performing a dehydration reaction on the intermediate. Alternatively, the compound (I) may be obtained by converting a hydroxyl group of the intermediate into another functional group such as halogen and then eliminating the functional group therefrom. Here, the usage amount of the above NaH is approximately equimolar to the compound (A), and the usage amount of n-BuLi is approximately 1.5 to 2.5 equivalent weights. Furthermore, the dehydration reaction and the elimination reaction of a functional group, which are described above, may be performed appropriately using conventionally well-known processes.

At the time of isolating the compound (I) produced by the above process, the isolation can be performed more easily when the above compound (I) is provided as a salt. Thus, the compound may be obtained as a salt. The salt of the compound (I) can be obtained as an acid-addition salt by adding an acid in an organic phase which is washed with water after the termination of a production reaction and separatory-extracted therefrom while optionally condensed and/or cooled, followed by stirring. Instead of acid, an ammonium salt and an amine addition salt can be obtained using ammonium and amines. When the compound (I) is obtained as a salt, it is preferable to eliminate a salt thereof at the time of subjecting the compound (I) to a reduction reaction using the microbial cells and/or a cell preparation thereof described below to obtain the compound (I).

The present invention is characterized in that in the compounds represented by the above formula (I) to (III), keto groups are stereo-selectively reduced using the microbial cells and/or a cell preparation thereof.

The microorganism to be used in the present invention is any microorganism as far as it is capable of stereo-selectively reducing a keto group.

More specifically, microorganisms belonging to the genus *Metschnikowia* such as *Metschnikowia pulcherrima, Metschnikowia bicuspidata, Metschnikowia reukaufii,* and *Metschnikowia lunata*; microorganisms belonging to the genus *Cryptococcus* such as *Cryptococcus curvatus, Cryptococcus flavus, Cryptococcus humicolus* and *Cryptococcus laurentii*; microorganisms belonging to the genus *Candida* such as *Candida albicans, Candida azyma, Candida intermedia, Candida solani, Candida famata, Candida guilliermondii, Candida parapsilosis, Candida rugosa, Candida tropicalis,* and *Candida molischiana*; microorganisms belonging to the genus *Filobasidium* such as *Filobasidium capsuligenum*; microorganisms belonging to the genus *Ogataea* such as *Ogataea glucozyma* and *Ogataea minuta*; microorganisms belonging to the genus *Citeromyces* such as *Citeromyces matritensis*; microorganisms belonging to the genus *Yarrowia* such as *Yarrowia lipolytica*; microorganisms belonging to the genus *Rhodotorula* such as *Rhodotorula glutinis, Rhodotorula aurantiaca,* and *Rhodotorula mucilaginosa*; microorganisms belonging to the genus *Exophiala* such as *Exophiala dermatitidis*; microorganisms belonging to the genus *Trigonopsis* such as *Trigonopsis variabilis*; microorganisms belonging to the genus *Shizosaccharomyces* such as *Shizosaccharomyces pombe*; microorganisms belonging to the genus *Wickerhamiella* such as *Wickerhamiella domercqii*; microorganisms belonging to the genus *Pichia* such as *Pichia petersonii* and *Pichia anomala*; microorganisms belonging to the genus *Saccharomycopsis* such as *Saccharomycopsis fibuligera* and *Saccharomycopsis crataegensis*; microorganisms belonging to the genus *Saitoella* such as *Saitoella complicata*; microorganisms belonging to the genus *Saccharomyces* such as *Saccharomyces cerevisiae*; microorganisms belonging to the genus *Rhodosporidium* such as *Rhodosporidium toruloides*; microorganisms belonging to the genus *Acinetobacter* such as *Acinetobacter calcoaceticus*; microorganisms belonging to the genus *Brevibacterium* such as *Brevibacterium linens,* and *Brevibacterium saccharolyticum*; microorganisms belonging to the genus *Cellulomonas* such as *Cellulomonas gelida, Cellulomonas flavigena,* and *Cellulomonas uda*; microorganisms belonging to the genus *Corynebacterium* such as *Corynebacterium ammoniagenes, Corynebacterium glutamicum, Corynebacterium acetoacidophilum, Corynebacterium vitaeruminis* and *Corynebacterium variabile*; and microorganisms belonging to the genus *Curtobacterium* such as *Curtobacterium flaccumfaciens* can be given.

As a specific example of the above-mentioned microorganisms, *Metschnikowia pulcherrima* IFO0863 strain, *Metschnikowia pulcherrima* IAM12196 strain, *Metschnikowia pulcherrima* IAM12197 strain, *Metschnikowia pulcherrima* IFO1407 strain, *Metschnikowia pulcherrima* IFO10796 strain, *Metschnikowia bicuspidata* IFO1408 strain, *Metschnikowia reukaufii* IFO10798 strain and *Metschnikowia lunata* IFO1605 strain; *Cryptococcus curvatus* IFO1159 strain, *Cryptococcus humicolus* IFO10250 strain, *Cryptococcus flavus* IFO0407 stain, *Cryptococcus laurentii* IFO0609 strain, *Cryptococcus laurentii* IFO1376 strain, *Cryptococcus laurentii* var *laurentii* CBS5539 strain, *Cryptococcus laurentii* var *laurentii* CBS2174 strain, *Cryptococcus laurentii* var *laurentii* CBS5746 strain, *Cryptococcus laurentii* var *laurentii* CBS7140 strain and *Cryptococcus laurentii* var *laurentii* CBS7235 strain; *Candida albicans* IFO1594 strain, *Candida azyma* JCM1691 strain, *Candida intermedia* IFO0761 strain, *Candida solani* IFO0762 strain, *Candida famata* RIFY7455 strain (also available as IFO0856 strain), *Candida guilliermondii* IFO0566 strain, *Candida parapsilosis* CBS0604 strain, *Candida rugosa* IFO0591 strain, *Candida tropicalis* IFO0618 strain, *Candida tropicalis* IFO1404 strain, *Candida tropicalis* IFO1647 strain, and *Candida molischiana* IFO10296 strain; *Filobasidium capsuligenum* IFO1119 strain, and *Filobasidium capsuligenum* IFO1185 strain; *Ogataea glucozyma* IFO1472 strain, and *Ogataea minuta* var *nonfermentans* IFO1473 strain; *Citeromyces matritensis* IFO0651 strain, and *Citeromyces matritensis* IFO0954 strain; *Yarrowia lipolytica* IFO1209 strain; *Rhodotorula glutinis* var *dairenensis* IFO0415 strain, *Rhodotorula glutinis* var *glutinis* IFO0395 strain, *Rhodotorula aurantiaca* IFO0754 strain, *Rhodotorula mucilaginosa* IFO0003 strain; *Exophiala dermatitidis* IFO6421 strain, and *Exophiala dermatitidis* IFO8193 strain, *Trigonopsis variabilis* CBS1040 strain and *Trigonopsis variabilis* IFO0671 strain; *Shizosaccharomyces pombe* IFO0344 strain, and *Shizosaccharomyces pombe* IFO1628 strain; *Wickerhamiella domercqii* IFO1857 strain; *Pichia petersonii* IFO1372 strain and *Pichia anomala* IFO0118 strain; *Saccharomycopsis fibuligera* IFO0105 strain and *Saccharomycopsis crataegensis* IFO1708 strain; *Saitoella complicata* IAM12963 strain; *Saccharomyces cerevisiae* JCM1818 strain, *Saccharomyces cerevisiae* IFO0565 strain and *Saccharomyces cerevisiae* IFO0305 strain; *Rhodosporidium toruloides* IFO0559 strain; *Acinetobacter calcoaceticus* IFO12552 strain; *Brevibacterium linens* JCM1328 strain and *Brevibacterium saccharolyticum* ATCC14066 strain; *Cellulomonas gelida* JCM1489 strain, *Cellulomonas flavigena* JCM1490 stain and *Cellulomonas uda* JCM1492 strain; *Corynebacterium ammoniagenes* JCM1305 strain, *Corynebacterium glutamicum* JCM1307 strain, *Corynebacterium glutamicum* ATCC12813 strain, *Corynebacterium glutamicum* ATCC13032 strain, *Corynebacterium glutamicum* ATCC13826 strain, *Corynebacterium glutamicum* ATCC14067 strain, *Corynebacterium acetoacidophilum* ATCC13870 strain, *Corynebacterium vitaeruminis* JCM1323 strain, and *Corynebacterium variabile* JCM2154 strain and *Curtobacterium flaccumfaciens* ATCC12813 strain are preferably given.

The above-mentioned microorganisms preferably belong to the genus *Metschnikowia*, the genus *Cryptococcus*, the genus *Candida*, the genus *Filobasidium*, the genus *Ogataea*, the genus *Citeromyces*, the genus *Rhodotorula*, the genus *Exophiala*, the genus *Shizosaccharomyces*, the genus

*Wickerhamiella*, the genus *Pichia*, the genus *Saccharomycopsis*, the genus *Saitoella*, the genus *Saccharomyces*, the genus *Rhodosporidium*, the genus *Brevibacterium* or the genus *Corynebacterium*.

Further, as the micoorganisms belonging to the genus *Metschnikowia*, *Metschnikowia pulcherrima* and *Metschnikowia reukaufii* are preferably given.

As the microorganisms belonging to the genus *Cryptococcus*, *Cryptococcus flavus*, *Cryptococcus humicolus* and *Cryptococcus laurentii* are preferably given.

As the microorganisms belonging to the genus *Candida*, *Candida intermedia*, *Candida solani*, *Candida famata* and *Candida molischiana* are preferably given.

As the microorganisms belonging to the genus *Filobasidium*, *Filobasidium capsuligenum* is preferably given.

As the microorganisms belonging to the genus *Ogataea*, *Ogataea glucozyma*, and *Ogataea minuta* are preferably given.

As the microorganisms belonging to the genus *Citeromyces*, *Citeromyces matritensis* is preferably given.

As the microorganisms belonging to the genus *Rhodotorula*, *Rhodotorula glutinis*, *Rhodotorula aurantiaca* and *Rhodotorula mucilaginosa* are preferably given.

As the microorganisms belonging to the genus *Exophiala*, *Exophiala dermatitidis* is preferably given.

As the microorganisms belonging to the genus *Shizosaccharomyces*, *Shizosaccharomyces pombe* is preferably given.

As the microorganisms belonging to the genus *Wickerhamiella*, *Wickerhamiella domercqiae* is preferably given.

As the microorganisms belonging to the genus *Pichia*, *Pichia petersonii* and *Pichia anomala* are preferably given.

As the microorganisms belonging to the genus *Saccharomycopsis*, *Saccharomycopsis fibuligera* is preferably given.

As the microorganisms belonging to the genus *Saitoella*, *Saitoella complicate* is preferably given.

As the microorganisms belonging to the genus *Saccharomyces*, *Saccharomyces cerevisiae* is preferably given.

As the microorganisms belonging to the genus *Rhodosporidium*, *Rhodosporidium toruloides* is preferably given.

As the microorganisms belonging to the genus *Brevibacterium*, *Brevibacterium saccharolyticum* is preferably given.

As the microorganisms belonging to the genus *Corynebacterium*, *Corynebacterium ammoniagenes*, *Corynebacterium glutamicum*, *Corynebacterium acetoacidophilum* and *Corynebacterium vitaeruminis* are preferably given.

Furthermore, when a compound represented by the formula (IV) is manufactured using a compound represented by the formula (I) as a raw material, an intermediate of the production may be prepared through a compound represented by the formula (II') or may be prepared through a compound represented by the formula (III').

In this case, the compound represented by the formula (II') and the compound represented by the formula (III') are produced from the compound represented by the formula (I) in advance. Then, they are isolated and introduced into the compound represented by the formula (IV). Alternatively, the compound represented by the formula (IV) may be produced directly without isolating the compound represented by the formula (II') and compound represented by the formula (III').

Furthermore, in the case of using the compound represented by the formula (I) as a raw material, the compound represented by the formula (IV) may be produced using one species of the microorganism, or two or more species of the microorganism may be used in combination for production.

As the material, microorganisms that are particularly preferable when using the compound represented by formula (I) are; microorganisms belonging to the genus *Cryptococcus*, the genus *Candida*, the genus *Filobasidium*, the genus *Ogataea*, the genus *Yarrowia*, the genuis *Rhodotorula*, the genus *Exophiala*, and the genus *Trigonopsis*; microorganisms belonging to the genus *Cryptococcus*, the genis *Candida*, the genus *Filobasidium*, the genus *Ogataea* and the genus *Rhodotorula* are more preferable, and microorganisms belonging to the genus *Ogataea* are most preferable.

As the material, microorganisms that are particularly preferable when using the compound represented by formula (II) are; microorganisms belonging to the genus *Metschnikowia*, the genus *Cryptococcus*, the genus *Candida*, the genus *Filobasidium*, the genus *Ogataea*, the genus *Citeromyces*, the genus *Yarrowia*, the genus *Rhodotorula*, the genus *Exophiala*, the genus *Trigonopsis*, the genus *Shizosaccharomyces*, the genus *Wickerhamiella*, the genus *Saccharomycopsis*, the genus *Saitoella*, the genus *Pichia*, the genus *Saccharomyces*, the genus *Rhodosporidium*, the genus *Acinetobacter*, the genus *Brevibacterium*, the genus *Cellulomonas*, the genus *Corynebacterium*, and the genus *Cartobacterium*.

The above-mentioned microorganisms more preferably belong to the genus *Metschnikowia*, the genus *Cryptococcus*, the genus *Candida*, the genus *Filobasidium*, the genus *Ogataea*, the genus *Citeromyces*, the genus *Rhodotorula*, the genus *Shizosaccharomyces*, the genus *Wickerhamiella*, the genus *Saccharomycopsis*, the genus *Saitoella*, the genus *Pichia*, the genus *Saccharomyces*, the genus *Rhodosporidium*, the genus *Brevibacterium* and the genus *Corynebacterium*; and the microorganisms belonging to the genus *Metschnikowla*, the genus *Candida*, the genus *Ogataea*, the genus *Rhodotorula*, the genus *Shizosaccharomyces*, the genus *Wickerhamiella*, the genus *Saccharomycopsis*, the genus *Saitoella*, the genus *Rhodosporidium*, the genus *Brevibacterium* and the genus *Corynebacterium* are even more preferable. The microorganisms belonging to the genus *Metschnikowa*, the genus *Candida*, the genus *Ogataea*, the genus *Shizosaccharomyces*, the genus *Saitoella*, the genus *Rhodosporidium*, the genus *Brevibacterium* and the genus *Corynebacterium* are most preferable.

As the material, microorganisms that are particularly preferable when using the compound represented by formula (III) are; microorganisms belonging to the genus *Cryptococcus*, the genus *Candida*, the genus *Filobasidium*, the genus *Rhodotorula*, and the genus *Pichia*; the microorganisms belonging to the genus *Cryptococcus*, the genis *Candida*, and the genus *Rhodotorula* are more preferable.

Note that, among the above microorganisms, microorganisms with the IFO numbers are described in an internet catalog (http://www.ifo.or.jp) published by the Institute for Fermentation, Osaka (IFO), and they are available from the IFO.

Microorganisms with the CBS numbers are described in an internet catalog (http://www.cbs.knaw.nl) of The Centraalbureau voor Schimmelcultures (CBS), and they are available from the CBS.

Microorganisms with the ATCC numbers are described in an internet catalog (http://www.atcc.org) of the American Type Culture Collection (ATCC), and they are available from the ATCC.

Microorganisms with the IAM numbers are described in an internet catalog (http://www.iam.u-tokyo.ac.jp/misyst/ColleBOX/IAMcollection.html) of the IAMCulture Collection (IAM), and they are available from the IAM.

Microorganisms with the JCM numbers are described in an internet catalog (http://www.jcm.riken.go.jp) of the Japan Collection of Microorganism (JCM), and they are available from the JCM.

Microorganisms with their respective RIFY numbers are described in a catalog of the Research Institute of Fermentation, Yamanashi Univ. Kofu Japan (RIFY), and they are available from the RIFY.

As the above microorganism, a mutant strain obtained by a conventional mutagenesis treatment such as an UV irradiation or an NTG treatment may be used as well as a wild strain. Alternatively, it may be any strain such as a recombinant strain induced by a genetic technique such as a cell fusion or a gene recombination.

In addition, as an expression strain of the recombinant strain, a bacterium such as a colon bacillus or yeast other than the original strain may be used, and their recombinant strains are also included in the concept of the above microorganism.

In the production process of the present invention, one species or two or more species of the above microorganisms are supplied to the reaction as microbial cells and/or a cell preparation thereof.

Specifically, the microbial cells obtained by culturing the above microorganism can be used without any treatment. Alternatively, a cell preparation obtained by treating the microbial cells, which are obtained by the culture, with a well-known technique such as an acetone treatment, a freeze-drying process, mechanical or enzymatical fragmentation of microbial cells or processed products thereof, or the like can be used. In addition, it is also possible to extract an enzyme fraction having a reduction ability from these microbial cells or a cell preparation thereof as a crude product or a purified product. Furthermore, it is also possible to use the microbial cells, the processed products of the microbial cells, the enzyme fraction, and so on obtained as described above, which are immobilized on a carrier such as a polyacrylamide or carrageenan gel using a conventional immobilization technique. In this specification, therefore, the term "microbial cells and/or a cell preparation thereof" is used as the concept including all of the above-described microbial cells, processed products of the microbial cells, enzyme fractions, and immobilized products thereof.

Next, the production process of the present invention will be specifically described.

In the production process of the present invention, a microorganism is generally used after incubation. This incubation can be performed by a general technique. A culture medium to be used for culturing the microorganism of the present invention includes a carbon source, a nitrogen source, inorganic ions, and so on, which can be assimilated by the microorganism. For the carbon source, carbohydrates such as glucose, fructose, and saccharose, polyalcohols such as glycerol, mannitol, and xylitol, organic acids, and so on are appropriately used. For the nitrogen source, organic nitrogen sources such as NZ amine, triptose, yeast extract, polypeptone, meat extract, and soybean extract, or inorganic nitrogen sources such as ammonium sulfate and ammonium nitrite are appropriately used. For the inorganic ions, a phosphate ion, a magnesium ion, an iron ion, a manganese ion, a molybdenum ion, and so on are used appropriately if required. Furthermore, it is effective to add inositol, pantothenic acid, nicotinamide, and other vitamins if required.

The contents of the above carbon source, nitrogen source, inorganic ions, and vitamins in the culture medium are not specifically limited as far as their contents are within their respective ranges typically used for the culture of a strain. The carbon source and the nitrogen source are added typically at a concentration of 0.001 to 50 wt %, preferably 0.1 to 5 wt %, respectively. The inorganic ions are added typically at a concentration of 0.0001 to 5 wt %, preferably 0.001 to 1 wt %. Vitamins are added typically at a concentration of 0.00001 to 10 wt %, more preferably 0.001 to 1 wt %.

The culture is performed for 1 to 100 hours under aerobic conditions, while adjusting pH within an appropriate range of about 3 to 11 and a temperature within an appropriate range of 4 to 50° C.

As a reaction process, a process by which the microorganism of the present invention is incubated, and the compound represented by each of the formulae (I) to (III) or a mixture thereof is added in an aqueous medium that contains the resulting microbial cells and/or a cell preparation thereof to obtain the objective compound represented by the formula (IV); a process by which the compound represented by each of the formulae (I) to (III) or a mixture thereof is added in the culture medium to perform the reaction while culturing the microorganism; a process by which after terminating the culture, the compound represented by each of the formulae (I) to (III) or a mixture thereof is added in the culture medium as it is, and the reaction is successively performed; a process by which the compound represented by the formula (I) is subjected to one of the above processes, and after the reaction proceeds to some extent, the microorganism separately cultured is additionally added on the basis of the contents of the compounds represented by the formulae (I) to (III) in the system; or the like, can be appropriately used.

For the above aqueous medium, a buffer using sodium phosphate, potassium phosphate, or the like is provided, and, in this buffer, the organic solvent, the surfactant, and so on are appropriately added.

The organic solvents include water-soluble solvents such as dimethyl sulfoxide (DMSO) and tetrahydrofuran (THF) and water-insoluble organic solvents such as butyl acetate and hexane. The surfactants include Tween 80, sugar ester, and so on.

The concentration of the buffer may be 1 M or less, preferably 0.2 M or less when in use.

The reaction may proceed at a temperature of 4 to 70° C., preferably 15 to 50° C., and at pH of 2 to 9, preferably 4 to 8.

The concentration of the respective compounds represented by the formulae (I) to (III) or a mixture thereof is in the range of 0.0001 to 10 wt %, preferably in the range of 0.001 to 5 wt % with respect to a reaction solution. If required, the compounds represented by the formulae (I) to (III) or a mixture thereof may be supplementally added during the reaction.

In addition, for accelerating the reaction, a co-enzyme, both of the co-enzyme and its regeneration system, or a carbon source may be appropriately added.

The co-enzymes typically include β-nicotinamide adenine dinucleotide, reduced form (hereinafter, abbreviated as NADH) or β-nicotinamide adenine dinucleotide phosphate, reduced form (hereinafter, abbreviated as NADPH). The addition amount thereof may be one-1000000th to 10 equivalent weights, preferably one-10000th to 10 equivalent weights of the reaction substrate.

The regeneration system of a co-enzyme may be a combination of an enzyme capable of reducing β-nicotinamide adenine dinucleotide (hereinafter, abbreviated as NAD) such as formic acid dehydrogenase into NADH and an enzyme substrate (formic acid), a combination of an enzyme capable of reducing β-nicotinamide adenine dinucleotide phosphate (hereinafter, abbreviated as NADP) such as glucose dehydrogenase into NADPH and an enzyme substrate (glucose or the like), or the like. These enzymes that regenerate the co-enzyme may be one commercially available, or may be a microbial cell and/or a cell preparation thereof having a regeneration ability of the co-enzyme. The addition amounts of these systems are suitably determined on the basis of the amount of the reaction substrate.

A carbon source for accelerating the above reaction may be any of carbon sources to be useful in the regeneration of a co-enzyme with the microbial cells and/or a cell preparation thereof to be used in the reaction. For instance, the carbon sources include carbohydrates such as glucose, fructose, and saccharose, and polyalcohols such as glycerol, mannitol, and xylitol, organic acids, and so on, and the addition amount thereof is 0.0001 to 50 wt %, preferably 0.01 to 10 wt %.

As described above, the reaction is performed using an aqueous medium. However, the compounds represented by the formulae (I) to (III) have low solubility in water, so that it is preferable to disperse the compound uniformly in the reaction system by dissolving or suspending it in an organic solvent, a surfactant, or the like upon the addition in advance.

For a compound represented by the formula (IV) obtained by the above production process, in general, impurities are removed by a conventional purification process, namely, a chromatography and a crystallizing technique after extracting the compound from a reaction solution with an organic solvent to obtain the purified compound represented by the formula (IV). Specifically, after dissolving the compound represented by the formula (IV) with an organic solvent, a solid fraction including a microorganism is eliminated by a conventional separator used in a centrifugation, a filter press, an ultrafiltration, etc. to obtain a liquid containing a compound represented by the formula (IV). Using the conventional method such as chromatography or crystallizing technique, impurities are removed from the resulting liquid. Thus, a purified compound represented by the formula (IV) can be obtained.

Hereinafter, the present invention will be described in more detail with reference to examples. However, general modifications can be performed in the technical field of the present invention without departing from the gist of the present invention.

In the meantime, (E)-7-[2-cyclopropyl-4-(4-fluorophenyl)-quinolin-3-yl]-3,5-dihydroxyhept-6-enic acid esters (hereinafter, abbreviated as "DOLE") have isomers: (3S, 5R)-isomer, (3R, 5R)-isomer, and (3S, 5S)-isomer, in addition to the objective (3R, 5S)-isomer. The structural formula is as follows.

3S, 5R-DOLE and 3R, 5S-DOLE are Syn isomers of DOLE, and 3S, 5S-DOLE and 3R, 5R-DOLE are anti isomers of DOLE.

In the examples, the purity of the (3R, 5S)-isomer which is the objective product is expressed by the excess diastereomer ratio and the excess enantiomer ratio. In this specification, the excess diastereomer ratio is represented by (syn-DOLE−anti-DOLE)/(syn-DOLE+ant-DOLE), and the excess enantiomer ratio is represented by (3R, 5S isomer−3S, 5R isomer)/(3R, 5S isomer+3S, 5R isomer).

Syn-DOLE

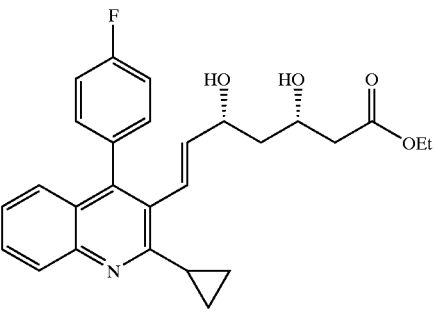

3S, 5R-DOLE

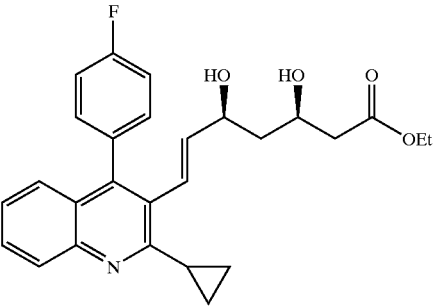

3R, 5S-DOLE anti-DOLE

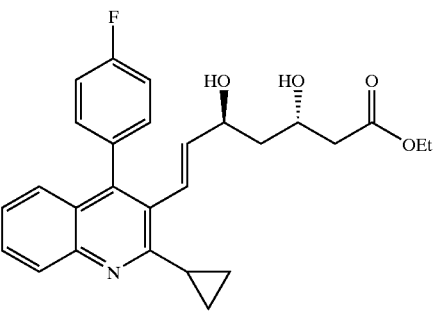

3S, 5S-DOLE

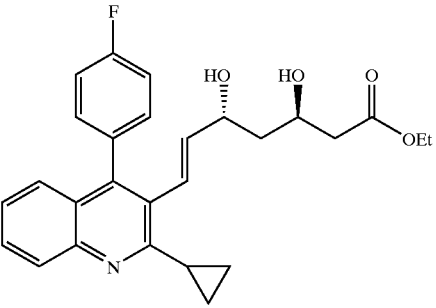

3R, 5R-DOLE

PRODUCTION EXAMPLE 1

Synthesis of (E)-7-[2-cyclopropyl-4-(4-fluorophenyl)-quinolin-3-yl]-3,5-dioxohept-6-enic acid ethyl ester (Hereinafter, Abbreviated as DOXE)

In a 500-ml four-neck flask equipped with a stirrer, a dropping funnel, and a thermo-meter, 5.02 g (11.22 mmol) of (E)-7-[2-cyclopropyl-4-(4-fluorophenyl)-quinolin-3-yl]-5-hydroxy-3-oxohept-6-enic acid ethyl ester (hereinafter, abbreviated as 5-MOLE) and 420 mL of acetone were added and stirred. Then, 10.5 mL of a prepared Jones oxidizing agent (i.e., a reagent obtained by mixing 3 mL of a concentrated sulfuric acid and 3.35 g of chromium oxide together, followed by diluting up to 25 mL with water) was dropped at 0° C. in 20 minutes, and was then stirred under ice cooling for 2 hours, followed by gently adding 10 mL of methanol to terminate the reaction. Subsequently, a reaction mixture solution was placed at reduced pressure to allow acetone to be distilled off, followed by the addition of 250 mL of ethyl acetate. The resulting solution was washed twice with 60 mL of saturated sodium bicarbonate aqueous solution, and was then washed twice with 60 mL of a saturated brine, followed by drying an ethyl acetate solution with anhydrous magnesium sulfate. Subsequently, the solvent was distilled off, and a purification was performed using a silica gel column chromatography (an eluting solvent; hexane:ethyl acetate= 2:1), resulting in 3.03 g of an entitled compound (yield: 60.6%).

$^1$H-NMR (300 MHz, CDCl$_3$, δppm): 7.79–7.19 (8H, m), 7.71 (1H, d), 6.03 (1H, d), 5.51 (1H, s), 4.21 (2H, q), 3.40 (2H, s), 2.35–2.40 (1H, m), 1.39–1.41 (2H, m), 1.28 (3H, t), 1.07–1.09 (2H, m).

PRODUCTION EXAMPLE 2

Synthesis of 5S-(E)-7-[2-cyclopropyl-4-(4-fluorophenyl)-quinolin-3-yl]-5-hydroxy-3-oxohept-6-enic acid ethyl ester (Hereinafter, Abbreviated as 5S-MOLE)

In a Schlenk tube introduced with nitrogen gas after being heated and dried at a reduced pressure, 0.87 g (3.3 mmol) of (S)-2-[N-(3,5-di-tert-butyl salicylidene) amino]-3-methyl-1-butanol, 5 ml of methylene chloride, and 0.63 ml (6.0 mmol) of titanium tetraethoxide were added, and stirred and mixed at a room temperature for 1 hour. After cooling the Schlenk tube down to −50° C., 0.95 g (3.0 mmol) of (E)-3-[2-cyclopropyl-4-(4-fluorophenyl)-quinolin-3-yl]-prop-2-en-1-al was dissolved in 2 ml of methylene chloride and was then dropped. After stirring it for 5 minutes, 0.51 g (6 mmol) of diketene was further added, and stirred for 22 hours while keeping the temperature at −50° C. for reaction. The resulting reaction mixture solution was added in a mixture solution of 25 ml of methylene chloride and 25 ml of a 0.24M sodium bicarbonate aqueous solution, and was mixed by being vigorously stirred for 2 hours at a room temperature to obtain a two-layer solution. The resulting two-layer solution was separated. A water layer was extracted twice with 10 ml of methylene chloride. The methylene chloride solution and the methylene chloride extract were combined together, resulting in a methylene chloride solution. The methylene chloride solution was dried with anhydrous magnesium sulfate, and the solvent was distilled off, followed by being purified with a silica gel column chromatography (an eluting solvent; hexane:ethyl acetate=3:2), resulting in 0.75 g of 5(S)-(E)-7-[2-cyclopropyl-4-(4-fluorophenyl)-quinolin-3-yl]-5-hydroxy-3-oxohept-6-enic acid ethyl ester (optical purity: 73% ee, and yield for (E)-3-[2-cyclopropyl-4-(4-fluorophenyl)-quinolin-3-yl]-prop-2-en-1-al: 56%).

PRODUCTION EXAMPLE 3

Synthesis of 7-[2-cyclopropyl-4-(4-fluorophenyl)-quinolin-3-yl]-7-hydroxy-3,5-dioxoheptanoic acid ethyl ester

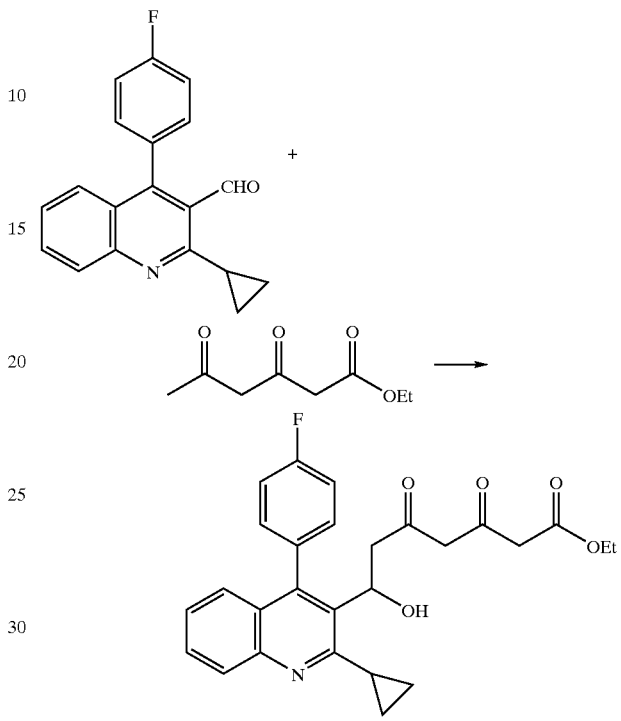

In a mixture solution of 2.40 g of an oily 60% sodium hydride and 200 ml of tetrahydrofuran, a mixture solution of 10.3 g of 3,5-dioxohexanoic acid ethyl ester and 40 ml of tetrahydrofuran was dropped in 20 minutes while keeping an inner temperature at 2° C. or less. After allowing a reaction for 50 minutes at −10° C., 75 ml of a hexane solution of 1.6 M n-butyl lithium was dropped in 40 minutes with the inner temperature kept at −20 to −15° C., while allowing a reaction for 40 minutes at an inner temperature of 2° C. or less. In this case, furthermore, while keeping an inner temperature of −15° C. or less, a mixture of 11.7 g of 2-cyclopropyl-4-(4-fluorophenyl)quinolin-3-carbaldehyde and 80 ml of tetrahydrofuran was dropped in 40 minutes and was then reacted at 10° C. or less for 1 hour. Furthermore, while keeping an inner temperature of 5° C. or less, 14.4 ml of acetic acid and 40 ml of toluene were added in a reaction system, followed by washing with 100 ml of water and 100 ml of saturated brine in that order. After the solvent is distilled off, the residue thus obtained was added with 100 ml of hexane and 5 ml of ethyl acetate so as to be crystallized, followed by filtrating and drying it to obtain 16.6 g (yield: 89%) of 7-[2-cyclopropyl-4-(4-fluorophenyl) quinolin-3-yl]-7-hydroxy-3,5-dioxoheptanoic acid ethyl ester was obtained.

NMR of the compound is as follows.

$^1$H-NMR (CDCl$_3$): 1.11 (2H, m), 1.13 (1H, m), 1.27 (3H, t, J=10), 1.76 (1H, m), 2.40 (1H, m), 2.48 (2H, ABq, J=66,14), 2.69 (2H, ABq, J=52,16), 2.78 (1H, m), 3.30 (1H, m), 4.18 (2H, m), 5.25 (1H, d, J=3), 5.58 (1H, dd, J=12,4), 7.16–7.26 (5H, m), 7.33 (1H, dd, J=7,7), 7.61 (1H, dd, J=7,7), 7.93 (1H, d, J=7)

PRODUCTION EXAMPLE 4

Synthesis of DOXE

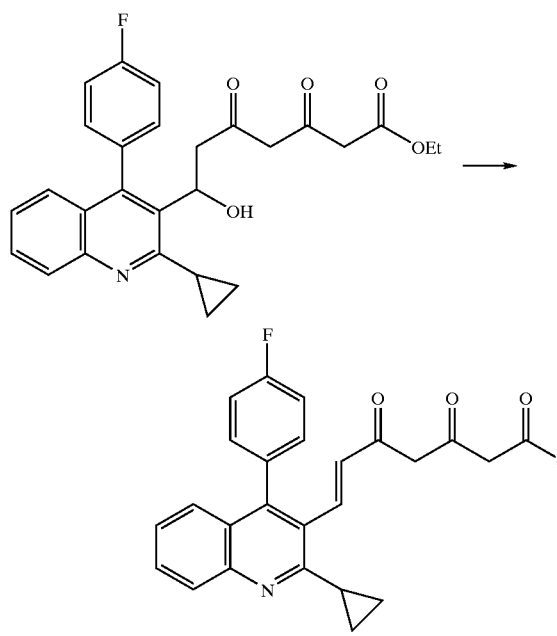

20.0 g of 7-[2-cyclopropyl-4-(4-fluorophenyl) quinolin-3-yl]-7-hydroxy-3,5-dioxoheptanoic acid ethyl ester obtained in Production Example 3 was dissolved in 120 ml of toluene. In addition, 10 g of silica gel and 8 g of anhydrous magnesium sulfate were added for the reaction for 16 hours at 95° C. After removing the silica gel and the inorganic salt from the reaction system, the solvent was distilled off, and the resulting residue was purified by a column chromatography (an eluting solvent; hexane:ethyl acetate=2:1), resulting in 8.4 g (yield 44%) of (E)-7-[2-cyclopropyl-4-(4-fluorophenyl) quinolin-3-yl]-3,5-dioxohept-6-enic acid ethyl ester (DOXE).

NMR of this compound is as follows.

$^1$H-NMR (CDCl$_3$): 1.09 (2H, m), 1.28 (3H, t, J=7), 1.40 (2H, m), 2.38 (1H, m), 3.40 (2H, s), 4.20 (2H, q, J=7), 5.51 (1H, s), 6.02 (1H, d, J=16), 7.16–7.26 (4H, m), 7.30–7.40 (2H, m), 7.70 (1H, d, J=16), 7.63 (1H, m), 7.97 (1H, m)

PRODUCTION EXAMPLE 5

Synthesis of DOXE

A mixture solution of 5.0 g of 7-[2-cyclopropyl-4-(4-fluorophenyl) quinolin-3-yl]-7-hydroxy-3,5-dioxoheptanoic acid ethyl ester obtained in Production Example 3, 10 ml of toluene, and 0.37 g of p-toluenesulfonic acid anhydride was reacted for 3 hours at 110° C. This reaction system was washed with sodium bicarbonate aqueous solution. Subsequently, the solvent was distilled, and a purification was performed using a column chromatography (an eluting solvent; hexane=ethyl acetate=2:1), resulting in 3.0 g (yield 63%) of (E)-7-[2-cyclopropyl-4-(4-fluorophenyl)quinolin-3-yl]-3,5-dioxohept-6-enic acid ethyl ester (DOXE).

PRODUCTION EXAMPLE 6

Synthesis of DOXE

A mixture solution of 0.50 g of 7-[2-cyclopropyl-4-(4-fluorophenyl) quinolin-3-yl]-7-hydroxy-3,5-dioxoheptanoic acid ethyl ester obtained in Production Example 3, 20 ml of toluene, and 0.037 g of p-toluenesulfonic acid anhydride was reacted for 1 hour at an inner temperature of 105° C. under a reduced pressure, while water generated during the reaction was distilled off by a component distillation with toluene. After recovering the pressure to normal pressure, 0.097 g of water was added in the reaction system to allow a reaction at 10 minutes at 90° C., followed by allowing the reaction for 1 hour under a reduced pressure while the water was distilled off at an inner temperature of 105° C. once more. The reaction system was analyzed using a high-performance liquid chromatography. It was confirmed that 0.37 g (yield 78%) equivalent of (E)-7-[2-cyclopropyl-4-(4-fluorophenyl)-quinolin-3-yl]-3,5-dioxohept-6-enic acid ethyl ester (DOXE) was produced.

PRODUCTION EXAMPLE 7

Synthesis of DOXE 0.01 g of sulfuric acid was added in a mixture solution of 0.2 g of 7-[2-cyclopropyl-4-(4-fluorophenyl) quinolin-3-yl]-7-hydroxy-3,5-dioxoheptanoic acid ethyl ester obtained in Production Example 3 and 2 ml of vinyl acetate, followed by reaction through reflux under heat for 5 hours. This reaction system was diluted with ethyl acetate, and was then washed with sodium bicarbonate aqueous solution. The solvent was distilled off, and the resulting residue was purified by a column chromatography (an eluting solvent; hexane:ethyl acetate=2:1), resulting in 0.14 g (yield 73%) of (E)-7-[2-cyclopropyl-4-(4-fluorophenyl)-quinolin-3-yl]-3,5-dioxohept-6-enic acid ethyl ester (DOXE).

PRODUCTION EXAMPLE 8

Synthesis of DOXE

A mixture solution of 2.0 g of 7-[2-cyclopropyl-4-(4-fluorophenyl) quinolin-3-yl]-7-hydroxy-3,5-dioxoheptanoic acid ethyl ester obtained in Production Example 3, 10 ml of acetic acid, 0.66 g of acetic anhydride, and 0.01 g of N,N-dimethyl-4-aminopyridine was reacted for 4 hours at 90° C. This reaction system was diluted with ethyl acetate, and was then washed with water and sodium bicarbonate aqueous solution. Thereafter, the solvent was distilled off, and the resulting residue was crystallized from hexane to obtain 1.55 g (yield 80%) of (E)-7-[2-cyclopropyl-4-(4-fluorophenyl)-quinolin-3-yl]-3,5-dioxohept-6-enic acid ethyl ester (DOXE).

PRODUCTION EXAMPLE 9

Synthesis of DOXE 0.250 g of 7-[2-cyclopropyl-4-(4-fluorophenyl) quinolin-3-yl]-7-hydroxy-3,5-dioxoheptanoic acid ethyl ester obtained in Production Example 3 was dissolved in 5 ml of 4 mol/L hydrochloric acid/ethyl acetate solution, and stirring was continued at 20° C. for 12 hours. The reaction system was analyzed by a high-performance liquid chromatography. It was confirmed that 0.198 g (yield 82%) equivalent of (E)-7-[2-cyclopropyl-4-(4-fluorophenyl)-quinolin-3-yl]-3,5-dioxohept-6-enic acid ethyl ester (DOXE) was generated.

PRODUCTION EXAMPLE 10

Synthesis of hydrochloride of DOXE

In a mixture solution of 1.37 g of an oily 60% sodium hydride and 10 ml of tetrahydrofuran, a mixture solution of 2.36 g of 3,5-dioxohexanoic acid ethyl ester and 10 ml of tetrahydrofuran was dropped in 5 minutes while keeping an inner temperature of 20° C. After stirring the mixture for 1 hour at that temperature, a mixture of 2.01 g of 2-cyclopropyl-4-(4-fluorophenyl)quinolin-3-carbaldehyde and 20 ml of tetrahydrofuran was dropped for 20 minutes. After stirring the mixture for 4 hours, a reaction solution was added in 3.09 g of acetic acid and 20 ml of water to terminate the reaction. An organic phase was extracted with 40 ml of ethyl acetate and was then washed with 20 ml of saturated brine, followed by being dried with 2 g of anhydrous sodium sulfate. As a result of analysis on the resulting organic phase, 2.52 g of (E)-7-[2-cyclopropyl-4-(4-fluorophenyl)quinolin-3-yl]-3,5-dioxohept-6-enic acid ethyl ester (DOXE) (yield 82%) was obtained.

After distilling the solvent off, 1.7 ml of 4 mol/L hydrochloric acid/ethyl acetate solution was added in the resulting residue at a room temperature. After the generation of a crystal, the temperature was lowered to 5° C. Then, the crystal was obtained through a filtration and was then dried, resulting in 2.49 g of hydrochloride (yield 75%) of (E)-7-[2-cyclopropyl-4-(4-fluorophenyl) quinolin-3-yl]-3,5-dioxohept-6-enic acid ethyl ester.

EXAMPLE 1

Production of DOLE from DOXE

Each kind of strains listed in Table 1 was inoculated in a liquid culture medium (2.5 mL) composed of 5 g/L of yeast extract (manufactured by Difco Co., Ltd.), 5 g/L of polypeptone (manufactured by Nihon Pharmaceutical Co., Ltd.), 3 g/L of malt extract (manufactured by Difco Co., Ltd.), and 20 g/L of glucose (manufactured by Nihon Shokuhinkako Co., Ltd.), and was then incubated at 30° C. for 21 hours under aerobic conditions. The resulting culture medium was centrifuged in an amount of 1 ml at a time to collect microbial cells. Then, 0.25 mL of a reaction solution containing the compound (I) (which is a compound, in the formula, R=ethyl group: DOXE) was added in the microbial cells to allow a reaction under aerobic conditions at 30° C. for 20 hours.

The composition of the above reaction solution includes 0.3 g/L of DOXE, 20 g/L of glucose(manufactured by Nihon Shokuhinkako Co., Ltd.), 20 mL/L of dimethyl sulfoxide (DMSO) (manufactured by Kishida Chemical Co., Ltd.), and a 100 mM potassium phosphate buffer (pH 7.0).

After terminating the reaction, 0.5 mL of ethyl acetate was added in the reaction solution and was mixed therewith vigorously, followed by separation into an organic layer and a water layer by a centrifugation. The organic layer was transferred to another container. A solvent was distilled off with a condensation centrifuge. Then, the dried solid product was dissolved in 0.01 mL of ethyl acetate, and was then subjected to a thin-layer chromatography (TLC). The TLC used a silica gel plate (silica gel 60 $F_{254}$ manufactured by Merck & Co.), and developing solvent used was of hexane/ethyl acetate=1/1.

After terminating the development, the product was confirmed with an UV lamp. As for the compound (I), Rf=0.76 to 0.86. As for compounds (II) and (III), Rf=0.54 to 0.61. As for the compound (IV) (which is a compound, in the formula, R=ethyl group: DOLE), Rf=0.33. A spot of the DOLE on the TLC was scraped and eluted with 0.25 mL of isopropanol. After the centrifugation, a supernatant was subjected to a high-performance liquid chromatography (HPLC) to analyze its optical purity and the concentration of a TLC-scraped-off sample.

The following is the conditions of HPLC.
Column: CHIRALCEL AD (manufactured by Daicel Chemical Industries, Ltd.)
Eluting solution: Hexane/ethanol=9/1
Flow rate: 0.5 ml/min.
Detection: UV 254 nm
Temperature: Room temperature
The results are listed in Table 1.

TABLE 1

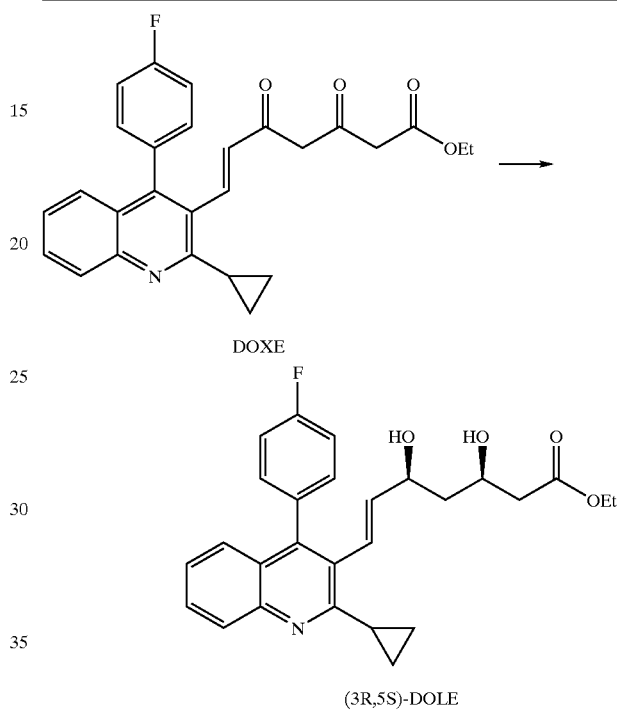

| Microorganism used | Concentration of TLC-scraped-off sample (Excess diastereomer ratio, excess enantiomer ratio) |
|---|---|
| *Candida famata* var *famata* RIFY7455 | 7.1 mg/L (97.1% d.e., 100.0% e.e.) |
| *Cryptococcus laurentii* IFO0609 | 0.4 mg/L (100.0% d.e., 100.0% e.e.) |
| *Filobasidiwn capsuligenum* IFO1185 | 2.7 mg/L (100.0% d.e., 100.0% e.e.) |
| *Ogataea minuta* var *nonfermentans* IFO1473 | 7.4 mg/L (92.0% d.e., 100.0% e.e.) |

EXAMPLE 2

Production of DOLE from DOXE

*Ogataea minuta* var *nonfermentans* IFO1473 was inoculated in 2.5 mL of a liquid culture medium having the same composition as that of Example 1, and was then incubated at 27° C. for each of 24 hours and 48 hours under aerobic conditions, respectively. The obtained culture solution was centrifuged in an amount of 1 ml at a time to collect microbial cells. Then, 0.2 ml of a 100 mM potassium phosphate buffer (pH 7.0) was added in the microbial cells to suspend them completely, followed by adding 20 μl of a 50% (w/v) glucose solution and 50 μl of a 5 g/L DOXE (DMSO solution) in the suspension and then stirring the mixture well to initiate a reaction for 20 hours at 27° C.

After terminating the reaction, an extraction with ethyl acetate and TLC were performed just as in the case of Example 1 and a spot of the DOLE on the TLC was scraped and eluted with 200 µl of isopropanol. After centrifugation, a supernatant was subjected to a high-performance liquid chromatography (HPLC) to analyze the optical purity thereof and the amount of the generation of DOLE.

The following is the conditions of HPLC.

Column: CHIRALCEL AD (manufactured by Daicel Chemical Industries, Ltd.)
Eluting solution: Hexane/ethanol=95/5
Flow rate: 1 ml/min.
Detection: UV 254 nm
Temperature: Room temperature The results are listed in Table 2.

TABLE 2

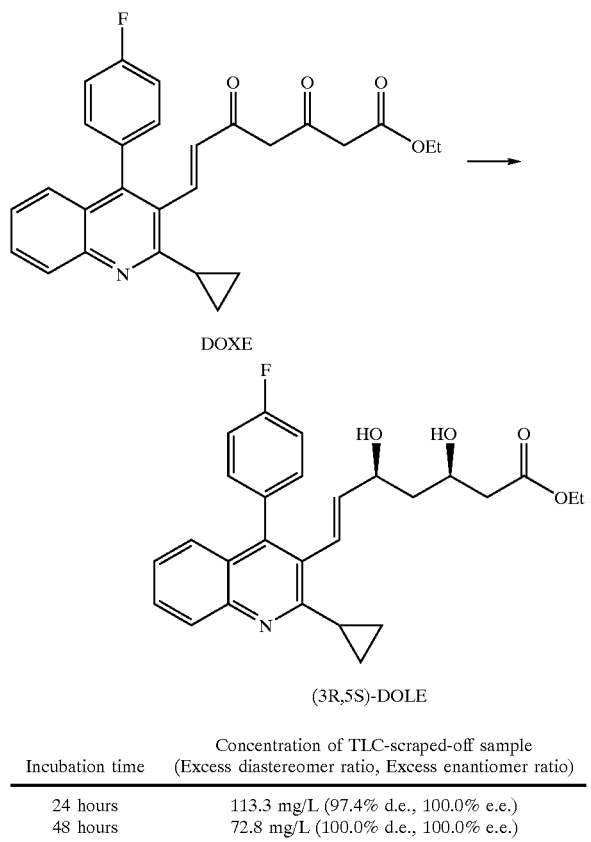

| Incubation time | Concentration of TLC-scraped-off sample (Excess diastereomer ratio, Excess enantiomer ratio) |
|---|---|
| 24 hours | 113.3 mg/L (97.4% d.e., 100.0% e.e.) |
| 48 hours | 72.8 mg/L (100.0% d.e., 100.0% e.e.) |

Furthermore, at the time of performing the above TLC, there was an Rf spot corresponding to 5-MOLE or 3-MOLE. Thus, only the spot of the 24-hour incubation was scraped off and was then subjected to the analysis on the amount of the generation using a high-performance liquid chromatography (HPLC).

The following is the conditions of HPLC.

Column: MCIGEL CHP2MGM (4.6×150 mm) (manufactured by Mitsubishi Chemical Corporation)
Eluting solution: Methanol/acetonitrile/water/phosphoric acid=800/100/100/0.5
Flow rate: 0.6 ml/min.
Detection: UV 254 nm
Temperature: 60° C.

Under this HPCL conditions, when the 5-MOLE had a retention time of 4.73 and the 3-MOLE had a retention time of 5.47, the TLC scraped-off sample concentration of the 5-MOLE was 25.2 mg/L, and the sample concentration of the 3-MOLE was 2.2 mg/L.

Incidentally, the DOLE had a retention time of 4.02 and the DOXE had a retention time of 8.02 under the above analysis conditions.

EXAMPLE 3

Production of MOLE from DOXE

*Rhodotorula aurantiaca* IFO0754 and *Rhodotorula glutinis* var dairenensis IFO0415 were respectively inoculated in 2.5 mL of a liquid culture medium having the same composition as that of Example 1. At 27° C. under aerobic conditions, *Rhodotorula aurantiaca* was incubated for 24 hours and *Rhodotorula glutinis* var dairenensis was incubated for 48 hours, respectively. The obtained culture solution was centrifuged in an amount of 1 ml at a time to collect microbial cells. Then, 0.2 ml of a 100 mM potassium phosphate buffer (pH 7.0) was added in the microbial cells to suspend them completely, followed by adding 20 µl of a 50%(w/v) glucose solution, 20 µl of a mixed solution of 2 g/L NADP and NAD, and 30 µl of a 10 g/L DOXE (DMSO solution) in the suspension and then stirring the mixture well to initiate a reaction for 12 hours at 27° C. under the aerobic conditions.

After terminating the reaction, the extraction with ethyl acetate and the TLC were performed in the same way as those of Example 1. An Rf spot portion corresponding to the 5-MOLE or the 3-MOLE and an Rf spot portion corresponding to the DOLE were scraped off, respectively.

Thereafter, DOLE and MOLE were analyzed using a high-performance liquid chromatography (HPLC) under the following conditions.

The following is the conditions of DOLE.

Column: CHIRALCEL AD (manufactured by Daicel Chemical Industries, Ltd.)
Eluting solution: Hexane/ethanol=95/5
Flow rate: 1 ml/min.
Detection: UV 254 nm
Temperature: Room temperature Further, the following is the conditions of MOLE.

Column: MCIGEL CHP2MGM (4.6×150 mm) (manufactured by Mitsubishi Chemical Corporation)
Eluting solution: Methanol/acetonitrile/water/phosphoric acid=800/100/100/0.5
Flow rate: 0.6 ml/min.
Detection: UV 254 nm
Temperature: 60° C.

The results are listed in Table 3.

TABLE 3

| Microorganism used | Concentration of TLC-scraped-off sample (each mg/L) | | |
|---|---|---|---|
| | 5-MOLE | 3-MOLE | DOLE |
| *Rhodotorula glutinis* var dairenensis IFO0415 | 44.9 | 2.2 | 2.9 (100% de, 100% ee) |
| *Rhodotorula aurantiaca* IFO0754 | 118.9 | N.D. | 15.3 (98.7% de, 100% ee) |

EXAMPLE 4

Production of 3-MOLE from DOXE

*Candida intermedia* IFO0761 was inoculated in 2.5 mL of a liquid culture medium having the same composition as that of Example 1. After incubating it at 27° C. for 24 hours, it was brought into a reaction with DOXE by the same operation as that of Example 2. Likewise, after the reaction, the extraction with ethyl acetate and the TLC were performed. An HPLC analysis on the spot revealed that the concentration of the TLC scraped-off sample of the 3-MOLE was 156.9 mg/L.

EXAMPLE 5

Production of 3-MOLE from DOXE

*Filobasidium capsuligenum* IFO1185 strain was inoculated in 2 L of a liquid culture medium having the same composition as that of Example 1 and incubated at 30° C. for 21 hours under aerobic conditions. The obtained culture solution was centrifuged and microbial cells were collected. A 10% (w/v) microbial cell suspension was prepared using a 10 mM potassium phosphate buffer (pH 7). Each 12-mL aliquot of the suspension was sampled into each of six tubes having a size of 30 φ. Then, 0.1 mL of 10% (w/v) DOXE (DMSO solution) and 0.15 ml of 50% (w/v) glucose solution were added in each tube to initiate a reaction at 30° C. for 20 hours under aerobic conditions.

After terminating the reaction, a reaction mixture was extracted using ethyl acetate. The extract was subjected to TLC under the same conditions as those of Example 1. A portion containing the compound (III) was scraped off. From the silica gel portion being scraped off, the extraction with ethyl acetate was performed, and the sample was analyzed by $^1$H-NMR.

$^1$H-NMR (400 MHz, CDCl$_3$, δppm): 1.02 (dt, J=6.4, 3.2 Hz, 2H), 1.21 (t, J=7.2 Hz, 3H), 1.33 (dt, J=6.4, 3.2 Hz, 2H), 2.26 (m, 1H), 2.43 (d, J=6.4 Hz, 2H), 2.60–2.66 (dd, J=6.4, 6.4 Hz, 2H), 3.37 (m, 1H), 4.11 (q, J=6.8 Hz, 2H), 4.34–4.41 (m, 1H), 6.27 (d, J=16.8 Hz, 1H), 7.06–7.36 (m, 6H), 7.52–7.62 (m, 1H), 7.60 (d, J=16.8 Hz, 1H), 7.90 (d, J=8.4 Hz, 1H)

From the results, the generation of 3-MOLE was confirmed.

Furthermore, the optical purity was analyzed using a high-performance liquid chromatography (HPLC) under the following conditions. As a result, it was found that the optical purity of the compound (III') was obtained at 87.3% ee.

The following is the conditions of HPLC in this example.
Column: CHIRALCEL AD (manufactured by Daicel Chemical Industries, Ltd.)
Eluting solution: Hexane/ethanol/trifluoroacetic acid=900/100/1
Flow rate: 1 ml/min.
Detection: UV 254 nm
Temperature: Room temperature

EXAMPLE 6

Production of DOLE and 3R-MOLE from DOXE 500-ml flasks each containing 50 mL of the liquid culture medium having the same composition as that of Example 1, were sterilized at 120° C. for 20 minutes, respectively. The eight flasks were inoculated with *Ogataea minuta* var *nonfermentans* IFO1473, followed by incubating it at 28° C. for 24 hours under aerobic conditions. The resulting culture solution corresponding to four of eight flasks was inoculated in each of two 30 L-jar fermentors, which contains 20 L of a liquid culture medium composed of 10 g/L of yeast extract (manufactured by Difco Co., Ltd.), 10 g/L of polypeptone (manufactured by Nihon Pharmaceutical Co., Ltd.), 6 g/L of malt extract (manufactured by Difco Co., Ltd.), and 20 g/L of glucose (manufactured by Nihon Shokuhinkako Co., Ltd.), followed by incubating them at 28° C. for 24 hours. After the incubation, the culture solution was centrifuged to collect microbial cells.

The microbial cells were completely suspended while being added in 9 L of a 100 mM potassium phosphate buffer (pH 7.0) and divided into three equal volumes. Then, each of them was placed in a 5 L-jar fermentor. In each fermentor, 53 g of glucose (manufactured by Nihon Shokuhinkako Co., Ltd.), 2 g of NADPH (manufactured by Oriental Yeast Co., Ltd.), and a solution in which 1.66 g of DOXE was dissolved in 130 ml of DMSO were added and reacted at 40° C. for 6 hours under aerobic conditions. Further, 2 g of NADPH was readded thereinto at a time 1 hour after the reaction. After the reaction, a part of a reaction solution in each fermentor was taken and the amount of the generation was analyzed using a high-performance liquid chromatography (HPLC). As a result, 3.43 g of DOLE was generated in total (yield 71%).

Each of the reaction solutions was centrifuged and precipitates were collected. In each of the precipitates, 600 ml of acetonitrile was added. After stirring the mixture sufficiently, a centrifugation was performed to separate the mixture into a supernatant and a precipitate. On the precipitate side, 200 ml of acetonitrile was additionally used for resuspension and centrifugation. All of supernatants were collected together and condensed with an evaporator. After the condensation, 600 ml of ethyl acetate was added, followed by washing with 50 ml of water twice after being dissolved.

An ethyl acetate layer was condensed and purified with a silica gel column chromatography. 400 ml of silica gel was placed in a column and was previously equilibrated with a solution of hexane:ethyl acetate=2:1. Then, a condensed sample was applied and 2 L of developing solvent of hexane:ethyl acetate=2:1 was fed. Subsequently, it was replaced with developing solvent of hexane:ethyl acetate=3:2, and 2 L thereof was fed to make an elution.

The eluted solution was divided into 200-ml fractions (20 in total). Each fraction was confirmed with TLC. The fractions in which the presence of DOLE was detected were collected and condensed, resulting in 3.4 g of crude oily DOLE. It was estimated in terms of purity, which corresponds to 2.5 g of DOLE.

The optical purity of the compound was investigated by an HPLC analysis under the conditions described in Example 2 above. In terms of an area ratio, 3S, 5R isomer:3R, 5R isomer:3R, 5S isomer:3S, 5S isomer= 0.3:0.2:98.9:0.6 (98.4% de, 99.4% ee).

On the other hand, when the fractions of the column purification, which correspond to portions where the 3-MOLE was detected as a main component, were collected, 1.5 g of crude oily product was obtained, so that 0.7 g of 3R-MOLE was obtained by subjecting it to another silica gel column chromatography for the purification again.

The optical purity was 98% ee when the same analysis as that of Example 2 was performed.

EXAMPLE 7

Production of DOLE from 5-MOLE

A reaction was performed by the same operation as that of Example 1, except for the use of various kinds of strains shown in Table 4 and 5-MOLE that contains R-5MOLE and S-5MOLE at a ratio of 1:1 as a reaction substrate instead of DOXE.

Among the products, DOLE, 3S, 5R isomer and 3R, 5R isomer are generated from 5R-MOLE, and 3R, 5S isomer and 3S, 5S isomer are generated from 5S-MOLE.

After terminating the reaction, the extraction with ethyl acetate and the TLC were performed as in the case of Example 1. Subsequently, a high-performance liquid chromatography (HPLC) was used for analyzing the optical purity and the amount of the generation.

The results are shown in Table 4.

TABLE 4

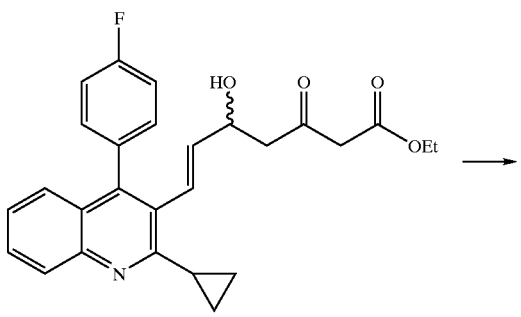

5-MOLE

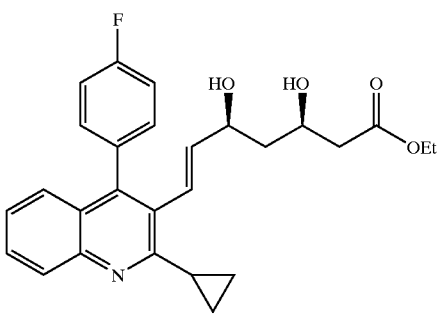

(3R,5S)-DOLE

| Microorganism used | Concentration of TLC-scraped-off sample (each mg/L) | | | | 3-position asymmetric reduction selectivity from 5S-MOLE | Excess enantiomer ratio (ee %) |
|---|---|---|---|---|---|---|
| | 3s,5r | 3r,5r | 3r,5s | 3s,5s | | |
| *Saccharomycopsis fibuligera* IFO0105 | 0.1, | 8.0, | 25.8, | 1.7 | 87.6% | 99.6% |
| *Wickerhamiella domercqii* IFO1857 | 0.2, | 16.7, | 16.0, | 1.4 | 83.9% | 97.3% |
| *Cryptococcus laurentii* var *laurentii* CBS5539 | 0.1, | 3.1, | 6.8, | 0.6 | 83.0% | 97.5% |
| *Metschnikowia pulcherrima* IFO10796 | 0.7, | 6.6, | 15.3, | 1.9 | 78.3% | 91.3% |
| *Metschnikowia pulcherrima* IFO1407 | 0.2, | 5.6, | 12.1, | 1.6 | 76.7% | 97.5% |
| *Ogataea minuta* var *nonfermentans* IFO1473 | 0.2, | 10.1, | 15.9, | 2.1 | 76.4% | 98.1% |
| *Exophiala dermatitidis* IFO8193 | 1.5, | 8.0, | 16.4, | 3.0 | 68.9% | 83.4% |
| *Filobasidium capsuligenum* IFO1185 | N.D., | 12.2, | 15.3, | 3.5 | 62.6% | 100.0% |
| *Rhodotorula glutinis* var *glutinis* IFO0395 | N.D., | 7.0, | 7.9, | 1.9 | 61.2% | 100.0% |
| *Candida famata* var *famata* IFO0856 | N.D., | 8.1, | 11.0, | 2.8 | 60.0% | 100.0% |
| *Pichia petersonii* IFO1372 | 0.1, | 1.0, | 3.3, | 0.8 | 59.2% | 92.3% |
| *Saccharomyces cerevisiae* IFO0565 | N.D., | 1.0, | 2.0, | 0.6 | 55.5% | 100.0% |

EXAMPLE 8

Production of DOLE from 5-MOLE

Each kind of strains listed in Table 5 was inoculated in 2.5 mL of a liquid culture medium composed of 10 g/L of yeast extract (manufactured by Difco Co., Ltd.), 8 g/L of polypeptone (manufactured by Nihon Pharmaceutical Co., Ltd.), 7 g/L of soybean extract HINUTE SMS (manufactured by Fuji Oil Co., Ltd.), 5 g/L of glucose (manufactured by Nihon Shokuhinkako Co., Ltd.), 10 g/L of glycerol (manufactured by Kishida Chemical Co., Ltd.), 1 g/L of potassium phosphate (manufactured by Wako Pure Chemical Industries, Ltd.), 3 g/L of dibasic potassium phosphate (manufactured by Wako Pure Chemical Industries, Ltd.), 0.5 g/L of magnesium sulfate (manufactured by Kishida Chemical Co., Ltd.), and 10 mg/L of manganese chloride (manufactured by Wako Pure Chemical Industries, Ltd.), and was then incubated at 30° C. for 24 hours under aerobic conditions. The resulting culture solution was centrifuged in an amount of 1 ml at a time and microbial cells were collected. Then, 0.2 ml of a 100 mM potassium phosphate buffer (pH 7.0) was added to suspend the microbial cells completely, followed by mixing with 10 μl of 50% (w/v) glucose solution, 10 μl of a mixture of 2 g/L-NADP (manufactured by Oriental Yeast Co., Ltd.) and NAD (manufactured by Oriental Yeast Co., Ltd.), and 10 μl of 5 g/L-DMSO solution of 5-MOLE in which R-5MOLE and S-5MOLE are contained at a ratio of 1:1. After stirred well, they were reacted at 30° C. for 20 hours under aerobic conditions.

After terminating the reaction, an extraction with ethyl acetate and TLC were performed just as in the case of Example 1 and a spot of the DOLE on the TLC was scraped and eluted in 200 μl of isopropanol. After centrifugation, a supernatant was subjected to a high-performance liquid chromatography (HPLC) to analyze the optical purity thereof and the amount of the generation of DOLE.

The following is the conditions of HPLC.

Column: CHIRALCEL AD (manufactured by Daicel Chemical Industries, Ltd.)
Eluting solution: Hexane/ethanol=95/5
Flow rate: 1 ml/min.
Detection: UV 254 nm
Temperature: Room temperature The results are listed in Table 5.

TABLE 5

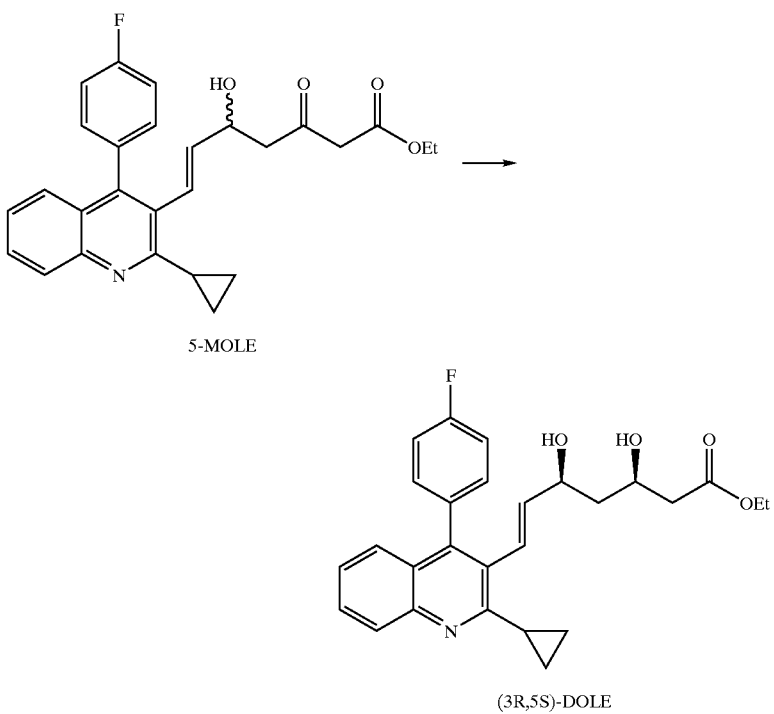

|  | Concentration of TLC-scraped-off sample (each mg/L) | | | | 3-position asymmetric reduction selectivity | Excess enantiomer |
| --- | --- | --- | --- | --- | --- | --- |
| Microorganism used | 3s,5r | 3r,5r | 3r,5s | 3s,5s | from 5S-MOLE | ratio (ee %) |
| *Corynebacterium glutamicum* ATCC14067 | N.D., | 95.7, | 54.1, | N.D. | 100.0% | 100.0% |
| *Corynebacterium glutamicum* ATCC13826 | N.D., | 112.1, | 22.1, | N.D. | 100.0% | 100.0% |

TABLE 5-continued

5-MOLE (3R,5S)-DOLE

| Microorganism used | Concentration of TLC-scraped-off sample (each mg/L) | | | | 3-position asymmetric reduction selectivity from 5S-MOLE | Excess enantiomer ratio (ee %) |
|---|---|---|---|---|---|---|
| | 3s,5r | 3r,5r | 3r,5s | 3s,5s | | |
| Corynebacterium ammoniagenes JCM1305 | N.D., | 119.9, | 72.8, | N.D. | 100.0% | 100.0% |
| Corynebacterium glutamicum JCM1307 | N.D., | 107.7, | 71.7, | N.D. | 100.0% | 100.0% |
| Brevibacterium saccharolyticum ATCC14066 | N.D., | 105.2, | 78.5, | N.D. | 100.0% | 100.0% |
| Corynebacterium acetoacidophilum ATCC13870 | 0.5, | 73.8, | 42.8, | N.D. | 100.0% | 97.7% |
| Corynebacterium glutamicum ATCC13032 | N.D., | 75.9, | 56.3, | N.D. | 100.0% | 100.0% |
| Corynebacterium vitaeruminis JCM1323 | 0.4, | 140.4, | 32.0, | N.D. | 100.0% | 99.4% |

EXAMPLE 9

Production of DOLE from 5-MOLE

Each kind of strains listed in Table 6 was inoculated in 2.5 mL of a liquid culture medium having the same composition as that of Example 1 and was incubated at 27° C. for 48 hours under the aerobic conditions. The resulting culture solution was centrifuged in an amount of 1 ml at a time and microbial cells were collected. Then, microbial cells were completely suspended by the addition of 0.2 ml of a 100 mM potassium phosphate buffer (pH 7.0). Subsequently, 20 μl of a 50% (w/v) glucose solution, and 50 μl of 5 g/L-DMSO solution of 5-MOLE including R-5MOLE and S-5MOLE at a ratio of 1:1 were added and stirred well, followed by reaction at 27° C. for 20 hours.

After terminating the reaction, an extraction with ethyl acetate and TLC were performed just as in the case of Example 8. After that, a high-performance liquid chromatography (HPLC) was used to analyze the optical purity and the amount of the generation.

The results are listed in Table 6.

TABLE 6

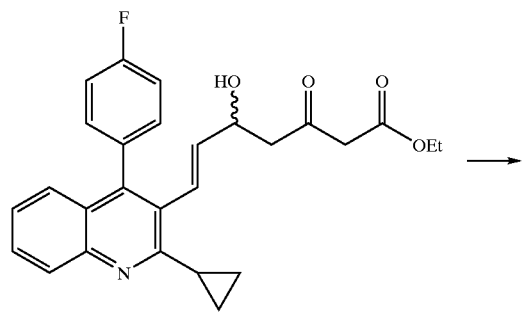

5-MOLE

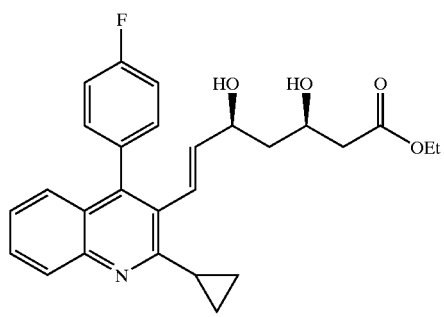

(3R,5S)-DOLE

| Microorganism used | Concentration of TLC-scraped-off sample (each mg/L) | | | | 3-position asymmetric reduction selectivity from 5S-MOLE | Excess enantiomer ratio (ee %) |
|---|---|---|---|---|---|---|
| | 3s,5r | 3r,5r | 3r,5s | 3s,5s | | |
| *Candida intermedia* IFO0761 | N.D., | 137.8, | 50.4, | N.D. | 100.0% | 100.0% |
| *Citeromyces matritensis* IFO0954 | N.D., | 4.7, | 9.9, | N.D | 100.0% | 100.0% |
| *Rhodotorula aurantiaca* IFO0754 | N.D., | 137.8, | 50.4, | N.D. | 100.0% | 100.0% |
| *Saitoella complicata* IAM12963 | 0.1, | 3.7, | 23.2, | N.D. | 100.0% | 99.1% |
| *Metschnikowia pulcherrima* IFO0863 | 1.4, | 47.9, | 100.6, | N.D. | 100.0% | 97.3% |
| *Metschnikowia pulcherrima* IFO10796 | 2.2, | 61.7, | 92.3, | N.D. | 100.0% | 95.3% |
| *Wickerhamiella domercqii* IFO1857 | 1.2, | 83.7, | 47.6, | N.D. | 100.0% | 95.1% |
| *Metschnikowia reukaufii* IFO10798 | N.D., | 43.9, | 79.1, | 0.2 | 99.5% | 100.0% |
| *Saccharomycopsis fibuligera* IFO0105 | 2.0, | 86.9, | 89.1, | 0.3 | 99.3% | 95.6% |
| *Ogataea glucozyma* IFO1472 | 0.5, | 169.6, | 221.1, | 1.4 | 98.7% | 99.5% |
| *Metschnikowia Pulcherrima* IFO1407 | N.D., | 37.4, | 75.3, | 0.5 | 98.7% | 100.0% |
| *Ogataea minuta* var *nonfermentans* IFO1473 | N.D., | 80.1, | 80.9, | 0.7 | 98.3% | 100.0% |
| *Rhodotorula glutinis* var *dairenensis* IFO0415 | 0.3, | 157.3, | 50.7, | 2.0 | 92.4% | 98.8% |
| *Pichia petersonii* IFO1372 | N.D., | 8.9, | 16.4, | 4.8 | 54.7% | 100.0% |

EXAMPLE 10

Production of DOLE from 5-MOLE

Each kind of strains listed in Table 7 was inoculated in 2 m+ of a liquid culture medium composed of 10 g/L of yeast extract (manufactured by DIfco Co., Ltd.), 5 g/L of Nutrient Broth (manufactured by DIfco Co., Ltd.), 3 g/L of soybean extract HINUTE SMS (manufactured by Fuji Oil Co., Ltd.), and 15 g/L of glucose (manufactured by Nihon Shokuhinkako Co., Ltd.), and was then incubated at 30° C. for 24 hours under aerobic conditions. The resulting culture solution was centrifuged in an amount of 1 ml at a time and microbial cells were collected. The same operation as that of Example 1 was performed, except that 5-MOLE containing R-5MOLE and S-5MOLE at a ratio of 1:1 was used as a reaction substrate for the microbial cells instead of DOXE.

After terminating the reaction, as in the case of Example 1, an extraction with ethyl acetate and TLC were performed, followed by a high-performance liquid chromatography (HPLC) to analyze the optical purity and the amount of the generation. The results are listed in Table 7.

TABLE 7

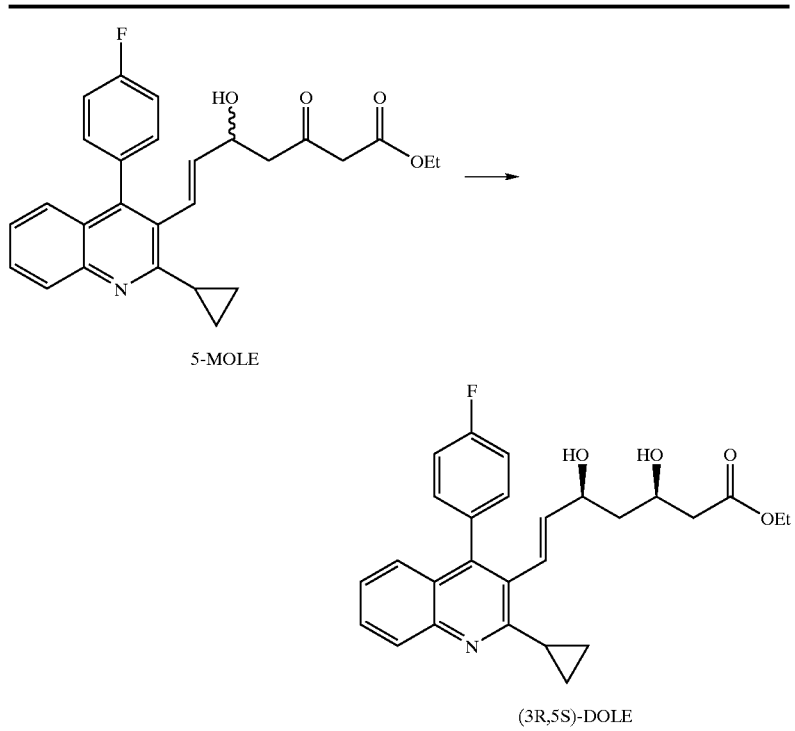

| Microorganism used | Concentration of TLC-scraped-off sample (each mg/L) | | | | 3-position asymmetric reduction selectivity from 5S-MOLE | Excess enantiomer ratio (ee %) |
| --- | --- | --- | --- | --- | --- | --- |
|  | 3s,5r | 3r,5r | 3r,5s | 3s,5s |  |  |
| *Acinetobacter calcoaceticus* IFO12552 | 3.0 | 6.6 | 63.8 | 26.6 | 41.2% | 91.0% |
| *Curtobacterium flaccumfaciens* ATCC12813 | 0.3 | 30.3 | 60.5 | 8.8 | 74.6% | 99.0% |
| *Cellulomonas flavigena* JCM1489 | 0.2 | 46.2 | 43.2 | 10.4 | 61.2% | 99.1% |
| *Cellulomonas gelida* JCM1490 | 0.2 | 51.1 | 38.2 | 10.5 | 56.9% | 99.0% |
| *Cellulomonas uda* JCM1492 | 1.0 | 37.1 | 53.1 | 8.8 | 71.6% | 96.3% |

EXAMPLE 11

Production of DOLE from 5S-MODE

Each kind of strains listed in Table 8 was incubated in the same way as that of Example 1. The resulting culture solution was centrifuged in an amount of 1 ml at a time and microbial cells were collected. Then, 0.25 ml of a 100 mM sodium phosphate buffer (pH 6.5) containing 5 g/L of glucose (Nihon Shokuhinkako Co., Ltd.), 60 μg/L of NADP (manufactured by Oriental Yeast Co., Ltd.), and 20 μg/L of glucose dehydrogenase (manufactured by Amano pharmaceutical Co., Ltd.: 73 units/mg) was added in the microbial cells to suspend them well.

In this suspension, 10 μl of DMSO that contains 10 g/L of 5S-MOLE having an optical purity of 73.0% ee, which was obtained according to Production Example 2, was added, followed by reaction at 30° C. for 20 hours under the aerobic conditions.

After terminating the reaction, an extraction with ethyl acetate and TLC were performed just as in the case of Example 1. After that, a high-performance liquid chromatography (HPLC) was used to analyze the optical purity and the amount of the generation.

The results are listed in Table 8.

TABLE 8

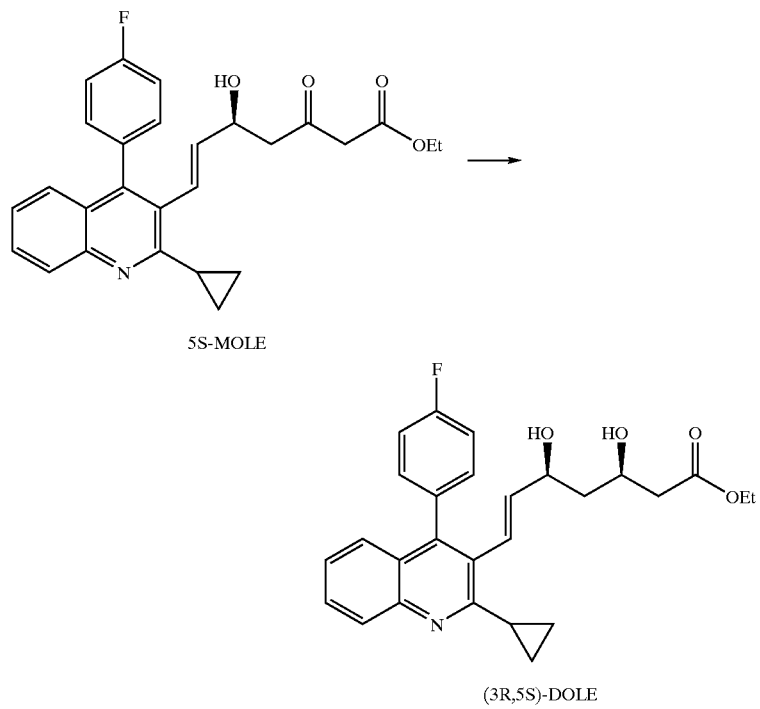

| Microorganism used | Concentration of TLC-scraped-off sample (Excess diastereomer ratio, excess enantiomer ratio) | 3-position asymmetric reduction selectivity from 5S-MOLE |
|---|---|---|
| *Saitoella complicate* IAM12963 | 13.28 mg/L (96.1% de, 96.6% ee) | 100.0% |
| *Candida solani* IFO0762 | 18.00 mg/L (94.7% de, 93.3% ee) | 100.0% |
| *Metschnikowia pulcherrima* IAM12197 | 38.53 mg/L (90.5% de, 97.8% ee) | 100.0% |
| *Shizosaccharomyces pombe* IFO0344 | 26.93 mg/L (88.3% de, 93.3% ee) | 96.6% |
| *Metschnikowia pulcherrima* IFO10796 | 12.62 mg/L (87.6% de, 97.2% ee) | 100.0% |
| *Ogataea glucozyma* IFO1472 | 87.69 mg/L (84.7% de, 98.4% ee) | 100.0% |
| *Ogataea minuta* var *nonfermentans* IFO1473 | 77.02 mg/L (79.4% de, 98.2% ee) | 100.0% |
| *Saccharomyces cerevisiae* IFO0565 | 1.67 mg/L (81.8% de, 78.4% ee) | 100.0% |
| *Saccharomyces cerevisiae* JCM1818 | 1.87 mg/L (77.0% de, 70.4% ee) | 100.0% |
| *Metschnikowia bicuspidate* IFO1408 | 11.76 mg/L (74.5% de, 94.3% ee) | 100.0% |
| *Shizosaccharomyces pombe* IFO1628 | 12.32 mg/L (74.1% de, 96.4% ee) | 96.4% |
| *Candida molischiana* IFO10296 | 36.72 mg/L (73.3% de, 94.7% ee) | 93.4% |
| *Rhodosporidium toruloides* IFO0559 | 20.27 mg/L (67.7% de, 95.7% ee) | 100.0% |
| *Candida famata* var *Famata* IFO0856 | 114.54 mg/L (64.0% de, 98.2% ee) | 93.0% |

TABLE 8-continued

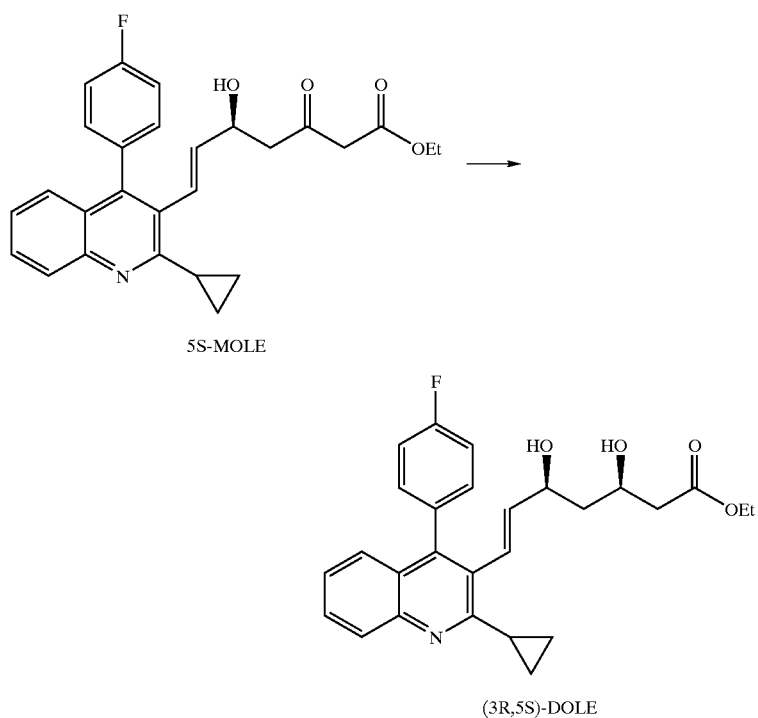

5S-MOLE (3R,5S)-DOLE

| Microorganism used | Concentration of TLC-scraped-off sample (Excess diastereomer ratio, excess enantiomer ratio) | 3-position asymmetric reduction selectivity from 5S-MOLE |
|---|---|---|
| *Filobasidium capsuligenum* IFO1185 | 116.20 mg/L (61.2% de, 98.6% ee) | 94.4% |
| *Citeromyces matritensis* IFO0954 | 6.02 mg/L (59.0% de, 82.0% ee) | 82.6% |
| *Cryptococcus humicolus* IFO10250 | 5.02 mg/L (58.9% de, 97.8% ee) | 100.0% |
| *Yarrowia lipolytica* IFO1209 | 0.90 mg/L (50.9% de, 56.6% ee) | 100.0% |
| *Candida intermedia* IFO0761 | 84.19 mg/L (49.4% de, 98.4% ee) | 89.7% |
| *Trigonopsis variabilis* CBS1040 | 7.89 mg/L (23.9% de, 91.9% ee) | 84.6% |

EXAMPLE 12

Production of DOLE from 3R-MODE

Each kind of strains listed in Table 9 was inoculated in 2.5 mL of a liquid culture medium having the same composition as that of Example 1 and was incubated at 27° C. for 48 hours under the aerobic conditions. The resulting culture solution was centrifuged in an amount of 1 ml at a time and microbial cells were collected. Then, microbial cells were completely suspended by the addition of 0.2 ml of a 100 mM sodium phosphate buffer (pH 7.0). Subsequently, 10 µl of 2 g/L of NADP (manufactured by Oriental Yeast Co., Ltd.) and NAD (manufactured by Oriental Yeast Co., Ltd.), 10 µl of a 25 units/ml-glucose dehydrogenase (manufactured by Amano pharmaceutical Co., Ltd.), 10 µl of a 50% (w/v) glucose solution, and 20 µl of 5 g/L-DMSO solution of 3R-MOLE prepared by Example 6 were added and stirred well, followed by reaction at 27° C. for 20 hours.

After terminating the reaction, an extraction with ethyl acetate and TLC were performed just as in the case of Example 8. After that, a high-performance liquid chromatography (HPLC) was used to analyze the optical purity and the amount of the generation.

The results are listed in Table 9.

TABLE 9

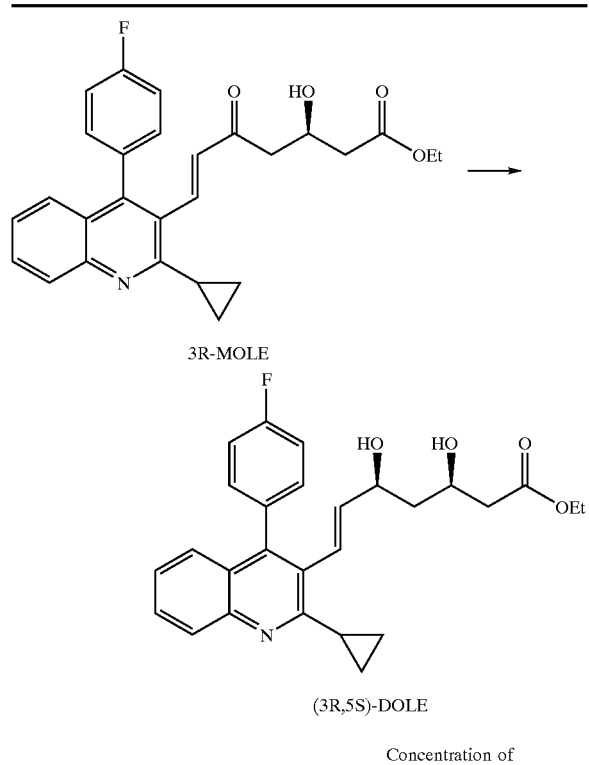

| Microorganism used | Concentration of TLC-scraped-off sample (mg/L) (Excess diastereomer ratio, excess enantiomer ratio) |
|---|---|
| *Candida famata* var *famata* IFO0856 | 59.9, (100% de, 100% ee) |
| *Filobasidiun capsuligenum* IFO1185 | 24.0, (100% de, 100% ee) |
| *Pichia anomala* IFO0118 | 1.0, (100% de, 100% ee) |
| *Pichia petersonii* IFO1372 | 2.8, (78.6% de, 100% ee) |
| *Cryptococcus laurentii* var *laurentii* CBS2174 | 23.8, (75.6% de, 100% ee) |
| *Cryptococcus laurentii* var *laurentii* CBS5746 | 40.4, (73.3% de, 100% ee) |
| *Cryptococcus laurentii* var *laurentii* CBS7140 | 32.4, (75.3% de, 100% ee) |
| *Cryptococcus laurentii* var *laurentii* CBS7235 | 18.9, (75.7% de, 100% ee) |
| *Cryptococcus flavus* IFO0407 | 36.7, (81.5% de, 100% ee) |
| *Rhodotorula mucilaginosa* IFO0003 | 81.5, (100% de, 100% ee) |
| *Rhodotorula glutinis* var *dairenensis* IFO0415 | 53.3, (83.9% de, 100% ee) |
| *Rhodotorula aurantiaca* IFO0754 | 108.6, (100% de, 100% ee) |

EXAMPLE 13

Production of DOLE from 3R-MODE

Each kind of strains listed in Table 10 was inoculated in 2.5 mL of a liquid culture medium having the same composition as that of Example 1 and was incubated at 27° C. for 48 hours under the aerobic conditions. The resulting culture solution was centrifuged in an amount of 1 ml at a time and microbial cells were collected. Then, microbial cells were completely suspended by the addition of 0.2 ml of a 100 mM sodium phosphate buffer (pH 7.0). Subsequently, 10 μl of 2 g/L of a mixed solution of NADP (manufactured by Oriental Yeast Co., Ltd.) and NAD (manufactured by Oriental Yeast Co., Ltd.), 10 μl of isopropanol, and 20 μl of 5 g/L-DMSO solution of 3R-MOLE prepared according to Example 6 were added and stirred well, followed by reaction at 27° C. for 20 hours.

After terminating the reaction, an extraction with ethyl acetate and TLC were performed just as in the case of Example 8. After that, a high-performance liquid chromatography (HPLC) was used to analyze the optical purity and the amount of the generation.

The results are listed in Table 10.

TABLE 10

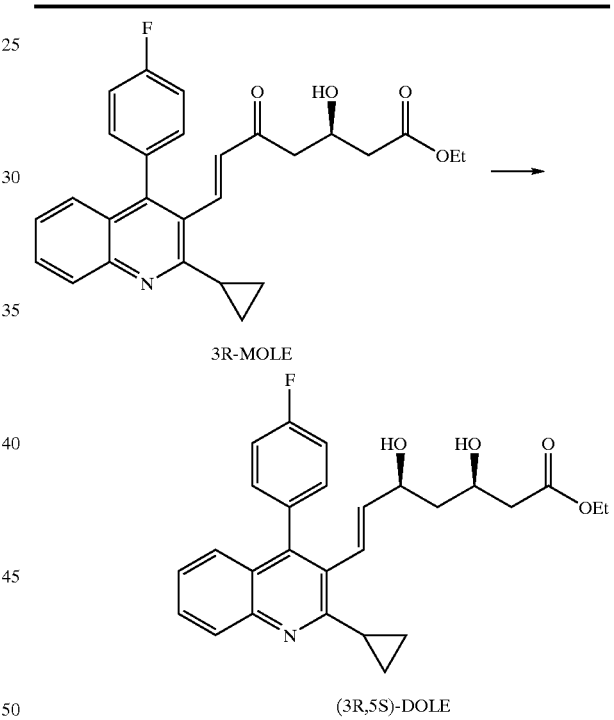

| Microorganism used | Concentration of TLC-scraped-off sample (mg/L) (Excess diastereomer ratio, excess enantiomer ratio) |
|---|---|
| *Cryptococcus laurentii* var *laurentii* CBS2174 | 51.3, (75.8% de, 100% ee) |
| *Cryptococcus laurentii* var laurentii CBS5746 | 29.3, (74.7% de, 98.4% ee) |
| *Cryptococcus laurentii* var *laurentii* CBS7140 | 79.8, (74.4% de, 100% ee) |
| *Cryptococcus laurentii* var laurentii CBS7235 | 88.4, (73.5% de, 99.2% ee) |
| *Rhodotorula mucilaginosa* IFO0003 | 97.3, (100% de, 100% ee) |
| *Rhodotorula glutinis* var *dairenensis* IFO0415 | 101.6, (83.9% de, 100% ee) |
| *Rhodotorula aurantiaca* IFO0754 | 91.6, (100% de, 100% ee) |

EXAMPLE 14

Production of DOLE from DOXE

In a 2.5 mL liquid culture medium having the same composition as that of Example 1, *Rhodotorula glutinis* variant dairenensis IFO0415 was inoculated and incubated at 27° C. for 48 hours under the aerobic conditions. The resulting culture solution in an amount of 1 ml was centrifuged, and microbial cells were collected.

Furthermore, in a 2.5 mL liquid culture medium having the same composition as that of Example 8, *Corynebacterium glutamicum* ATCC13826 was inoculated and incubated at 30° C. for 24 hours under aerobic conditions. The centrifugation was made on 1 ml of the obtained culture solution to collect the cells.

Both were combined together, in which 0.2 ml of a 100 mM potassium phosphate buffer (pH 7.0) was added to completely suspend them, and 10 µl of a mixture solution of 2 g/L of NADP (manufactured by Oriental Yeast Co., Ltd.) and NAD (manufactured by Oriental Yeast Co., Ltd.), 10 µl of 50% (w/v) glucose solution, and 30 µl of 20 g/L DOXE (DMSO solution) were mixed and stirred well, followed by reaction at 27° C. for 18 hours.

After terminating the reaction, an extraction with ethyl acetate and TLC were performed just as in the case of Example 1. After that, under the same conditions as those of Example 8, a high-performance liquid chromatography (HPLC) was used to analyze the optical purity and the amount of the generation. As a result, 3R, 5S-DOLE was only obtained in this reaction. Here, a concentration of a TLC-scraped-off sample was 9.5 mg/L.

EXAMPLE 15

Production of DCOOH from DOXE

Each kind of strains shown in Table 11 was incubated for reaction in the same way as that of Example 1. A spot (developing solvent; hexane:ethyl acetate=1:1, Rf=0) corresponding to the compound (IV) (which is a compound, in the formula, R=hydrogen: hereinafter, abbreviated as DCOOH) on the TLC was scraped off and was then eluted with 0.25 mL of isopropanol. After centrifugation, a high-performance liquid chromatography (HPLC) was used to analyze the supernatant.

The following is the conditions of HPLC.

Column: CHIRALCEL AD (manufactured by Daicel Chemical Industries, Ltd.)
Eluting solution: Hexane/ethanol/trifluoroacetic acid=900/100/1
Flow rate: 1 ml/min.
Detection: UV 254 nm
Temperature: Room temperature The results are listed in Table 11.

TABLE 11

| Microorganism used | Concentration of TLC-scraped-off sample (mg/L) (Excess diastereomer ratio, excess enantiomer ratio) |
|---|---|
| *Candida famata* RIFY7455 | 1.3, (94.0% d.e., 100.0% e.e.) |
| *Candida parapsilosis* CBS604 | 0.3, (100.0% d.e., 100.0% e.e.) |
| *Candida albicans* IFO1594 | 0.7, (81.8% d.e., 100.0% e.e.) |
| *Candida tropicalis* IFO0618 | 1.1, (89.6% d.e., 100.0% e.e.) |
| *Candida tropicalis* IFO1404 | 0.6, 100.0% d.e., 100.0% e.e.) |
| *Filobasidium capsuligenum* IFO1185 | 3.8, (94.7% d.e., 100.0% e.e.) |
| *Yarrowia lipolytica* IFO1209 | 0.7, (92.5% d.e., 100.0% e.e.) |
| *Trigonopsis variabilis* CBS1040 | 0.9, (79.2% d.e., 100.0% e.e.) |
| *Cryptococcus curvatus* IFO1159 | 14.5, (87.3% d.e., 100.0% e.e.) |
| *Cryptococcus humicolus* IFO10250 | 2.1, (100.0% d.e., 100.0% e.e.) |

EXAMPLE 16

Production of DCOOH from 5-MOLE

Each kind of strains shown in Table 12 was incubated in the same way as that of Example 1, except that 5-MOLE was used instead of DOXE. A spot (developing solvent; hexane:ethyl acetate=1:1, Rf=0) corresponding to the compound (IV) (which is a compound, in the formula, R=hydrogen: hereinafter, abbreviated as DCOOH) on the TLC was scraped off and was then eluted with 0.25 mL of isopropanol. After centrifugation, a supernatant was subjected to a high-performance liquid chromatography (HPLC) under the same conditions as those of Example 15, to analyze the optical purity. The results are listed in Table 12.

TABLE 12

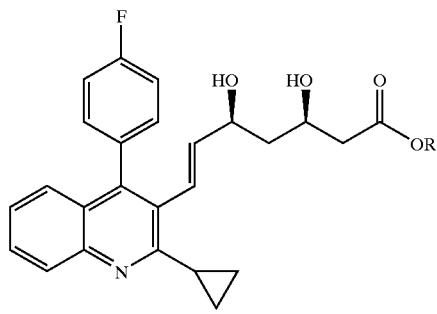

| Microorganism used | Concentration of TLC-scraped-off sample (mg/L) (Excess diastereomer ratio, excess enantiomer ratio) |
|---|---|
| *Candida rugosa* IFO0591 | 0.5, (85.6% d.e., 100.0% e.e.) |
| *Candida molischiana* IFO10296 | 1.8, (71.9% d.e., 100.0% e.e.) |
| *Candida parapsilosis* CBS604 | 2.8, (71.8% d.e., 100.0% e.e.) |
| *Cryptococcus laurentii* IFO0609 | 0.1, (100.0% d.e., 100.0% e.e.) |
| *Exophiala dermatitidis* IFO6421 | 9.9, (71.4% d.e., 100.0% e.e.) |
| *Exophiala dermatitidis* IFO8193 | 5.2, (73.1% d.e., 100.0% e.e.) |
| *Trigonopsis variabilis* IFO0671 | 0.5, (89.9% d.e., 100.0% e.e.) |

INDUSTRIAL APPLICABILITY

According to the present invention, 3R, 5S-(E)-7-[2-cyclopropyl-4-(4-fluorophenyl)-quinolin-3-yl]-3,5-dihydroxyhept-6-enic acid esters can be efficiently produced with high optical purities.

What is claimed is:

1. A process for producing a compound represented by the following formula (IV):

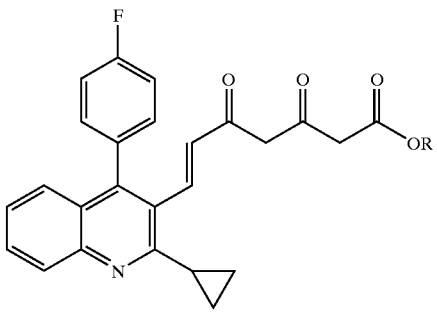

wherein R denotes a hydrogen atom, an alkyl group, or an aryl group, comprising reducing a compound selected from the group consisting of:

a compound represented by the following formula (I):

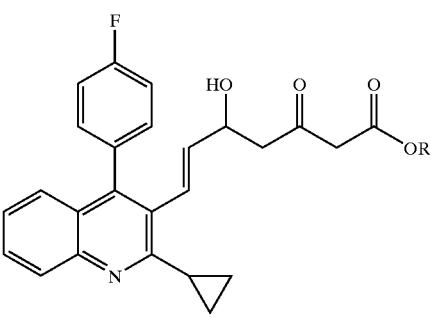

wherein R is as defined in the formula (IV);

a compound represented by the following formula (II):

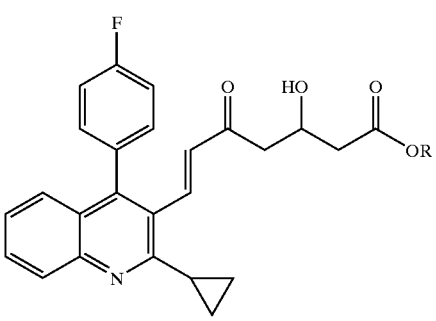

wherein R is as defined in the formula (IV); and a compound represented by the following formula (III):

III wherein R is as defined in the formula (IV), by reacting the compound with microbial cells and/or a cell preparation of a microorganism capable of stereoselectively reducing a keto group, wherein the microorganism is select from the group consisting of the genera *Metschnikowia, Cryptococcus, Candida, Filobasidium, Ogataea, Citeromyces, Yarrowia, Rhodotorula, Exophiala, Trigonopsis, Shizosaccharomyces, Wickerhamiella, Pichia, Saccharomycopsis, Saitoella, Saccharomyces, Rhodosporidium, Acinetobacter, Brevibacterium, Cellulomonas, Corynebacterium*, and genus *Curtobacterium*.

2. The process according to claim 1, wherein the compounds represented by the formulae (II) and (III) are optically active substances each represented by the following formula (II'):

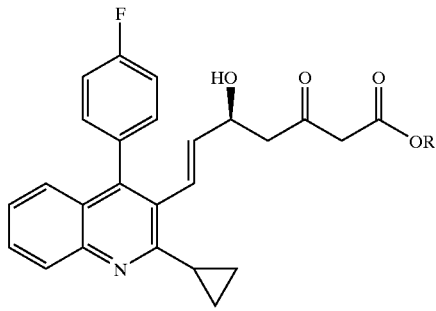

II' wherein R is as defined in the formula (IV), and the following formula (III'):

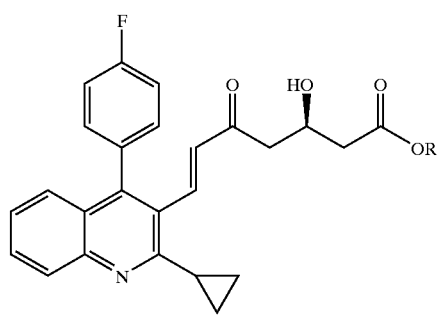

III' wherein R is as defined in the formula (IV).

3. The process according to claim 2, wherein each of the compounds represented by the formula (II') and the formula (III') is obtained from the compound represented by the formula (I).

4. The process according to claim 1, wherein the microorganism is selected from the group consisting of the genera *Metschnikowia, Cryptococcus, Candida, Filobasidium, Ogataea, Citeromyces, Rhodotorula, Exophiala, Shizosaccharomyces, Wickerhamiella, Pichia, Saccharomycopsis, Saitoella, Saccharomyces, Rhodosporidium, Brevibacterium*, and *Corynebacterium*.

5. The process according to claim 1, wherein the compound represented by the following formula (I):

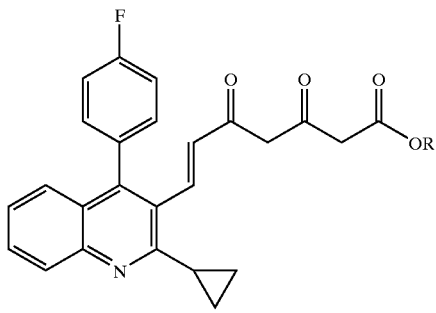

I wherein R is as defined in the formula (IV), is reacted with the microorganism selected from the group consisting of the genera *Cryptococcus, Candida, Filobasidium, Ogataea, Yarrowia, Rhodotorula, Exophiala*, and *Trigonopsis*.

6. The process according to claim 5, wherein the microorganism is selected from the group consisting of the genera *Cryptococcus, Candida, Filobasidium, Ogataea*, and *Rhodotorula*.

7. The process according to claim 1, wherein the compound represented by the following formula (II):

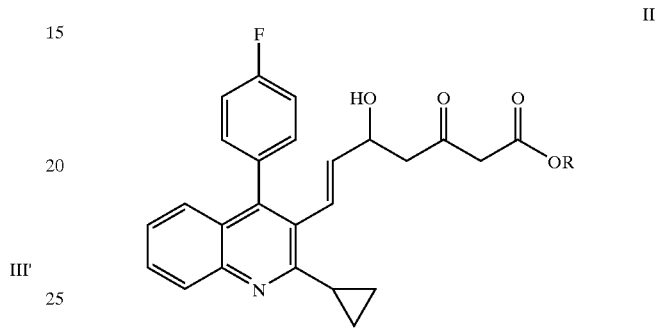

II wherein R is as defined in the formula (IV), is reacted with the microorganism selected from the group consisting of the genera *Metschnikowia, Cryptococcus, Candida, Filobasidium, Ogataea, Citeromyces, Yarrowia, Rhodotorula, Exophiala, Trigonopsis, Shizosaccharomyces, Wickerhamiella, Saccharomycopsis, Saitoella, Pichia, Saccaromyces, Rhodosporidium, Acinetobacter, Brevibacterium, Cellulomonas, Corynebacterium*, and *Curtobacterium*.

8. The process according to claim 7, wherein the microorganism is selected from the group consisting of the genera *Metschnikowia, Cryptococcus, Candida, Filobasidium, Ogataea, Citeromyces, Rhodotorula, Shizosaccharomyces, Wickerhamiella, Saccharomycopsis, Saitoella, Pichia, Saccharomyces, Rhodosporidium, Brevibacterium*, and *Corynebacterium*.

9. The process according to claim 1, wherein the compound represented by the following formula (III):

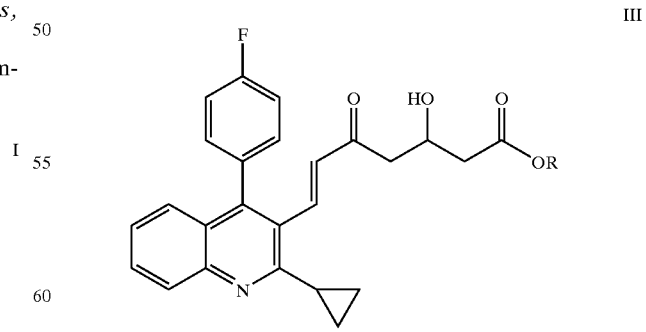

III wherein R is as defined in the formula (IV), is reacted with the microorganism selected from the group consisting of the genera *Cryptococcus, Candida, Rhodotorula, Filobasidium*, and *Pichia*.

10. The process according to claim 2, wherein the compound represented by the following formula (II'):

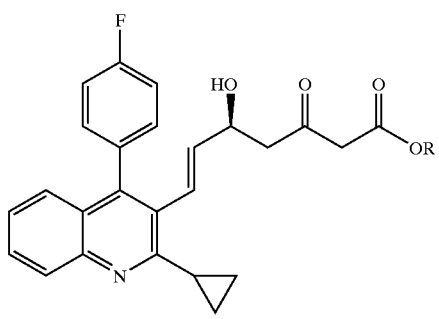

wherein R is as defined in the formula (IV),
is reacted with the microorganism selected from the group consisting of the genera *Metschnikowia, Cryptococcus, Candida, Filobasidium, Ogataea, Citeromyces, Yarrowia, Rhodotorula, Exophiala, Trigonopsis, Shizosaccharomyces, Wickerhamiella, Saccharomycopsis, Saitoella, Pichici, Saccaromyces, Rhodosporidium, Acinetobacter, Brevibacterium, Cellulomonas, Corynebacterium,* and *Curtobacterium.*

11. The process according to claim 3, wherein the compound represented by the following formula (II'):

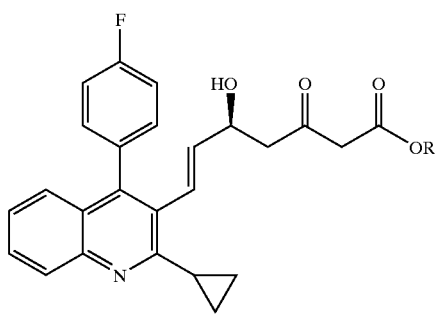

wherein R is as defined in the formula (IV),
is reacted with the microorganism selected from the group consisting of the genera *Metschnikowia, Cryptococcus, Candida, Filobasidium, Ogaaea, Citeromyces, Yarrowia, Rhodotorula, Exophiala, Trigonopsis, Shizosaccharomyces, Wickerhamiella, Saccharomycopsis, Saitoella, Pichia, Saccaromyces, Rhodosporidium, Acinetobacter, Brevibacterium, Cellulomonas, Corynebacierium,* and *Curtobacterium.*

12. The process according to claim 2, wherein the compound represented by the following formula (III'):

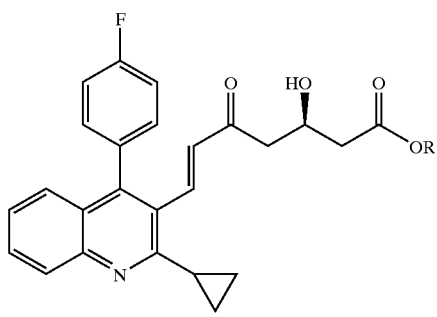

wherein R is as defined in the formula (IV),
is reacted with the microorganism selected from the group consisting of the genera *Cryprococcus, Candida, Rhodotorula, Filobasidium,* and *Pichia.*

13. The process according to claim 3, wherein the compound represented by the following formula (III'):

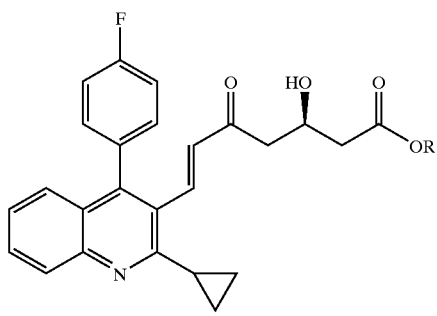

wherein R is as defined in the formula (IV),
is reacted with the microorganism selected from the group consisting of the genera *Cryptococcus, Candida, Rhodotorula, Filobasidium,* and *Pichia.*

* * * * *